United States Patent
Van Dyke et al.

(10) Patent No.: US 7,829,108 B2
(45) Date of Patent: Nov. 9, 2010

(54) STRUCTURALLY MODIFIED ACELLULAR TISSUE ENGINEERING SCAFFOLDS AND METHODS OF PRODUCTION

(75) Inventors: Mark E. Van Dyke, Winston-Salem, NC (US); George J. Christ, Winston-Salem, NC (US); Patrick W. Whitlock, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 25 days.

(21) Appl. No.: 11/738,258

(22) Filed: Apr. 20, 2007

(65) Prior Publication Data

US 2007/0248638 A1    Oct. 25, 2007

(51) Int. Cl.
*A61K 9/00* (2006.01)

(52) U.S. Cl. ........................ 424/422; 424/423; 424/469; 424/472

(58) Field of Classification Search ......... 424/422–423, 424/469, 472
See application file for complete search history.

(56) References Cited

U.S. PATENT DOCUMENTS

| | | | |
|---|---|---|---|
| 6,376,244 B1 | 4/2002 | Atala | |
| 6,689,161 B2 * | 2/2004 | Chen et al. | 623/1.43 |
| 6,753,181 B2 | 6/2004 | Atala | |
| 6,866,686 B2 | 3/2005 | Ollerenshaw et al. | |
| 6,893,653 B2 | 5/2005 | Abraham et al. | |
| 6,893,666 B2 | 5/2005 | Spievack | |
| 6,933,103 B1 | 8/2005 | Klein et al. | |
| 6,962,814 B2 | 11/2005 | Mitchell et al. | |
| 6,998,418 B1 | 2/2006 | Sung et al. | |
| 7,087,089 B2 | 8/2006 | Patel et al. | |
| 7,108,721 B2 | 9/2006 | Huckle et al. | |
| 7,201,917 B2 | 4/2007 | Malaviya et al. | |
| 2003/0026787 A1 | 2/2003 | Fearnot et al. | |
| 2006/0275377 A1* | 12/2006 | Gomes et al. | 424/569 |

OTHER PUBLICATIONS

Badylak SF, The extracellular matrix as a scaffold for tissue reconstruction, Semin. Cell Dev. Biol. 13(5):377-383 (2002).
Poehling GG et al., Analysis of outcomes of anterior cruciate ligament repair with 5-year follow-up: allograft versus autograft, Arthroscopy 21(7):774-785 (2005).
Whitlock PW et al., A naturally derived, cytocompatible, and architecturally optimized scaffold for tendon and ligament regeneration, Biomaterials Jul. 3, 2007 [Epub ahead of print].
International Search Report and Written Opinion, PCT/US07/09781, mailed Oct. 2, 2008.
Whitlock PW et al. A naturally derived, cytocompatible, and architecturally optimized scaffold for tendon and ligament regeneration. Biomaterials. 2007; 28: 4321-4329.

* cited by examiner

*Primary Examiner*—Ruth A Davis
(74) *Attorney, Agent, or Firm*—Myers Bigel Sibley & Sajovec, P.A.

(57) ABSTRACT

Methods are provided for producing a bioscaffold from natural tissues by oxidizing a decellularized tissue to produce a bioscaffold having pores therein. The pore size and porosity is increased to better accommodate intact cells so that live cells can better infiltrate and inhabit the bioscaffold. The bioscaffold may be freeze-dried or lyophilized, sterilized and (optionally) aseptically packaged for subsequent use. A further aspect of the present invention is a bioscaffold produced by the processes described herein. Methods of treatment using the bioscaffold as a graft or as a biomedical implant for implantation are also provided. Also provided are methods of seeding a bioscaffold with mammalian cells, wherein the seeding carried out either in vitro or in vivo, and wherein a bioscaffold produced as described herein is utilized for said seeding.

21 Claims, 14 Drawing Sheets

Untreated

Treated

|  | Freeze-dried Achilles | Scaffold | % ↓ | p-value |
|---|---|---|---|---|
| DNA Content (ug DNA / mg tissue; x ± SD) | 0.40 ± 0.14 | 0.11 ± 0.02 | ~75% | <0.05 |
Figure 9
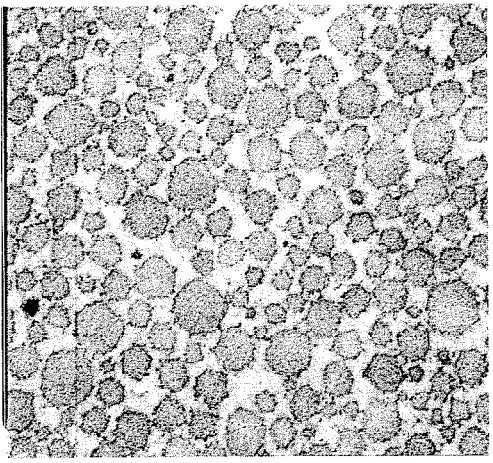
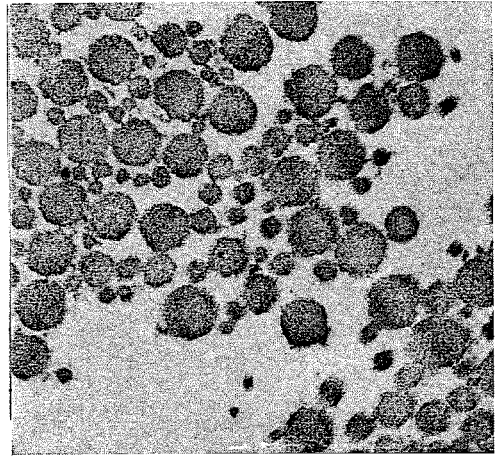
Figure 10A          Figure 10B

|  | *Cells Exposed to Media Only (+ Control) 72 h | Scaffold 72h | % of + Control | p-value |
|---|---|---|---|---|
| MTS™ Assay (Abs at 490 ηm; x ± SD) | 1.42 ± 0.31 | 1.36 ± 0.17 | ~95% | >0.05 |
| Neutral Red Assay (Abs at 540 ηm; x ± SD) | 0.24 ± 0.07 | 0.22 ± 0.07 | ~92% | >0.05 |

STRUCTURALLY MODIFIED ACELLULAR TISSUE ENGINEERING SCAFFOLDS AND METHODS OF PRODUCTION

RELATED APPLICATIONS

This application claims the benefit under 35 U.S.C. §119 (e) of U.S. Provisional Patent Application Ser. No. 60/794, 037, filed Apr. 21, 2006, the disclosure of which is incorporated herein by reference in its entirety.

FIELD OF THE INVENTION

The present invention concerns tissue engineering scaffolds and methods of making the same.

BACKGROUND OF THE INVENTION

Bioscaffold engineering has the potential to vastly improve the treatment of tissue injuries, especially those associated with tumor, trauma, and congenital deficiencies where autograft tissue (i.e., tissue harvested from the recipient patient) or allograft tissue (i.e., tissue harvested from a different subject of the same species) might not be available in sufficient quantity for reconstruction. Current tissue-engineering strategies have relied on scaffolds derived from both synthetic (e.g., polyglycolic acid) and naturally-derived (e.g., collagen) materials to form the cell-scaffold construct. Currently available tissue scaffold products include small intestine submucosa (Restore™, porcine SIS, DePuy Orthopaedics), (CuffPatch™, porcine SIS, Organogenesis), (SIS; Cook Biotech, Inc.), reformulated collagen scaffolds (3D Collagen Composite, BD Biosciences), acellular human dermal collagen matrices (Graftjacket®, Wright Medical Technologies), fetal bovine dermis (TissueMend®, Stryker), and synthetic polymer scaffolds, primarily polyesters (e.g. PGA, PCL, and PLA).

Synthetic scaffolds can produce breakdown products that have been shown to be antimitotic and cytotoxic in vivo (Garvin et al. (2003) *Tissue Eng* 9(5):967-979). Many synthetic and naturally-derived scaffolds also lack the initial mechanical strength to permit immediate motion and rehabilitation after implantation, leading to subsequent adhesion formation, decreased range of motion, and poor functional outcomes (Cao et al. (2002) *Plast Reconstr Surg* 110:1280-1289; Buckwalter (1996) *Hand Clin* 12(1):13-24; Buckwalter (1995) *Iowa Orthop J* 15:29-42). As an example, tissue engineered tendons produced in vitro have been shown to be weaker than native adult tendons and would not be expected to withstand rehabilitation after implantation (Garvin et al. (2003) *Tissue Eng* 9(5):967-979; Calve et al. (2004) *Tissue Eng* 10(5/6):755-761).

Tendon allografts (i.e., tissue taken from an animal of the same species but not of the same genotype) are useful in ligamentous reconstruction due to their availability and lack of donor site pathology (Poehling et al. (2005) *Arthroscopy* 21(7):774-85; Cole et al. (2005) *Arthroscopy* 21(7):786-90). However, these grafts have a micro-architecture that is quite dense and in which appreciable amounts of cellular debris remain, even in freeze-dried grafts. Experience in the preparation and use of allogeneic and xenogeneic (i.e., tissue taken from an animal of a different species) grafts for tissue regeneration has shown that dense grafts with residual cells are difficult to seed in vitro, instigate prolonged inflammatory responses in vivo, and require longer times to incorporate into native tissue and remodel. In clinical practice, this phenomenon has been observed using human allograft tissue and has been shown to result in a delay of remodeling and integration of implanted allografts in comparison to autograft tissue (Jackson et al. (1996) *Clin Orthop Rel Res* 324:126-33).

Most current strategies for the development of tissue-engineered tendons and ligaments have relied on a construct consisting of cells seeded onto a scaffold. However, the products of recent in vivo and in vitro studies have not produced a construct with sufficient biomechanical strength to withstand immediate rehabilitation after implantation. It is widely accepted that controlled early restoration of activity can promote healing of soft-tissue injuries and that the prolonged rest or immobilization of soft-tissue injuries can result in delayed recovery and permanent loss of function (Buckwalter (1996) *Hand Clin* 12(1): 13-24; Buckwalter (1995) *Iowa Orthop J* 15:29-42).

Methods for removing cells from tissues to create a porous bioscaffold are documented (see, e.g., Badylak (2002) *Semin Cell Dev Biol* 13(5):377-83; U.S. Pat. No. 6,893,666; U.S. Pat. No. 6,962,814; U.S. Pat. No. 6,893,653; U.S. Pat. No. 6,866,686; U.S. Pat. No. 6,753,181; U.S. Pat. No. 6,933,103). A typical method uses a hypo-osmotic solution such as deionized water to burst the cells, followed by a detergent solution, perhaps in combination with an enzyme for disrupting cell adhesion, to remove the cellular debris. A third step is often extraction with a mild basic solution to remove anionic materials such as DNA. The detergent and basic solution are often combined into a single step for convenience. These methods are effective for removal of cellular material without disrupting the native architecture of the extracellular matrix (ECM) or removing many biologically active molecules that mediate cell attachment and growth.

However, because the cells are essentially broken into small fragments and washed away, the porosity of these bioscaffolds is not ideal for repopulating with new cells, whether they are provided via in vitro seeding or by host cell infiltration. This is particularly true if the bioscaffold originated from a dense organ or tissue such as muscle, tendons, ligaments, nerve, blood vessel, cartilage, etc. In fact, most tissues contain a degree of compartmentalization that creates barriers to cell migration. Consequently, seeding cells uniformly throughout such bioscaffolds is extremely difficult, and in some cases impossible.

In addition, ingrowth of seeded or host cells proceeds via a cell-mediated remodeling process that requires considerable time. When a cell seeding approach is used, the subject cells typically attach only to the outside of the bioscaffold and grow outward, away from the bioscaffold.

There remains a need for an improved bioscaffold that addresses these problems and provides an ideal substrate on which cells can grow.

SUMMARY OF THE INVENTION

A first aspect of the invention is a method of producing a bioscaffold by decellularizing a tissue to produce a bioscaffold having pores therein. The method incorporates an additional step of oxidizing the bioscaffold during the decellularizing step with an oxidant (e.g., hydrogen peroxide, peracetic acid), with the oxidant preferably being in an aqueous solution, to remove extraneous extracellular matrix material and increase the average pore size therein (for example, in some embodiments, by increasing the average pore size by at least 20, 30, 40 or 50 percent or more). In preferred embodiments, the decellularizing step also includes a detergent.

The average pore size is increased to better accommodate intact cells so that live cells can better re-inhabit the bioscaffold. In some embodiments, the average size of the pores formed after the oxidizing step is at least 10, 20, or 30 microns, or in some embodiments at least 50 or 100 microns or more, depending upon the particular cells which are eventually desired to seed into and populate the scaffold.

Preferably, the advential layer or capsular layer on the tissue is removed (completely, at least in part, or at least a major portion thereof), prior to the decellularizing step, or between the decellularizing and oxidizing step, or after the oxidizing step, so that cell seeding efficiency is facilitated when cells are seeded (in vitro before implantation or in vivo after implantation) on the bioscaffold.

The method preferably includes the step of washing said bioscaffold (e.g., with water, saline solution, buffer solution or the like) after said oxidizing step to remove residual oxidant.

The bioscaffold may be freeze-dried or lyophilized after the oxidizing step, sterilized and (optionally) aseptically packaged for subsequent use.

A further aspect of the present invention is a bioscaffold produced by the processes described herein. The bioscaffold preferably has an average pore size that is at least 20, 30, 50, or 100% greater than the average pore size of said extracellular matrix component of said natural animal tissue prior to said treating; and wherein said natural animal tissue is selected from the group consisting of skin, muscle, tendon, bone, meniscus, cartilage, intervertebral discs, and ligament tissue.

Methods of treatment using the bioscaffold as a graft or as a biomedical implant for implantation are provided. The bioscaffold is grafted or implanted in an appropriate configuration into a subject in need thereof, with the particular manner of grafting or implantation depending upon the particular type of tissue being used and the particular condition being treated. Particular applications of the products of the present invention include cardio-vascular tissue engineering, nerve tissue engineering, musculoskeletal tissue engineering, bone, meniscus and cartilage tissue engineering, 3-D cell culture systems, and bioreactor systems.

A further aspect of the present invention is a method of seeding a bioscaffold with mammalian cells (e.g., human, dog, cat, pig, cow, rat, mouse cells, etc.) said seeding carried out either in vitro or in vivo, wherein a bioscaffold produced as described herein is utilized for said seeding.

Another aspect of the present invention is the use of a bioscaffold as described herein for the preparation of a graft or transplant for carrying out a method of treatment as described herein.

The present invention is explained in greater detail in the drawings herein and the specification set forth below.

BRIEF DESCRIPTION OF THE DRAWINGS

FIG. 5A: Metabolic Activity Assay (MTS Assay). Metabolic activity for cells exposed to the decellularized/oxidized FDP tendon scaffold is 79% of that observed for cells exposed to media only (control) and was statistically significant ($p<0.05$, abs at $\lambda=490$ nm+/−SEM, two-tailed, Student's t-test with unequal variances). FIG. 5B: Neutral Red Assay. Cell viability for cells exposed to the decellularized/oxidized FDP tendon scaffold is 88% of that observed for cells exposed to media only (control), which was not statistically significant ($p>0.05$, abs at $\lambda=540$ nm+/−SEM, two-tailed, Student's t-test with unequal variances).

FIG. 8A: Untreated Achilles tendon allograft, midsubstance, longitudinal section, 100×. Left: H&E staining, Right: DAPI staining. FIG. 8B: Treated Achilles tendon allograft, midsubstance, longitudinal section, 100×. Left: H&E staining, Right: DAPI staining.

FIG. 9. DNA content of the decellularized/oxidized freeze-dried human Achilles tendon allograft-derived scaffolds was significantly decreased by 75% (0.110+/−0.02 µg DNA/mg tissue dry weight, n=10) after treatment when compared to untreated freeze-dried human Achilles tendon allografts (0.40+/−0.14 µg DNA/mg tissue dry weight, n=10), $p<0.05$ FIGS. 10A-10B. Transmission electron microscopy of untreated (FIG. 10A) and treated (FIG. 10B) human Achilles tendon allograft, 51,000×. Microscopy revealed a decrease in fibril density per unit area after treatment of the freeze-dried human Achilles tendon allograft, which represents an increase on pore size and porosity of the scaffold.

FIG. 11. Mitochondrial activity determined using the MTS assay (absorbance at $\lambda=490$ nm) for NIH 3T3 cells exposed to the decellularized/oxidized freeze-dried human Achilles tendon allograft-derived scaffolds was 95% (1.36+/−0.31, n=10) of that observed for cells exposed to media only (1.42+/−0.31, n=10) a difference which was not statistically significant ($p>0.05$). Cell viability determined using the Neutral Red assay (absorbance at $\lambda=540$ nm) for NIH 3T3 cells exposed to the decellularized/oxidized freeze-dried human Achilles tendon allograft-derived scaffolds was 92% (0.24+/−0.07, n=10) of that observed for NIH 3T3 cells exposed to media alone (0.22+/−0.07, n=10, positive control), a difference which was not statistically significant. The decellularized/oxidized scaffold and positive control (cells only) differed significantly (p<0.001) from the values obtained for a known cytotoxic material (latex, negative control, n=10) in both assays. The absorbance observed for the negative control was also <10% of the absorbance observed for positive controls in each assay.

DETAILED DESCRIPTION OF THE PREFERRED EMBODIMENTS

Figure 1:
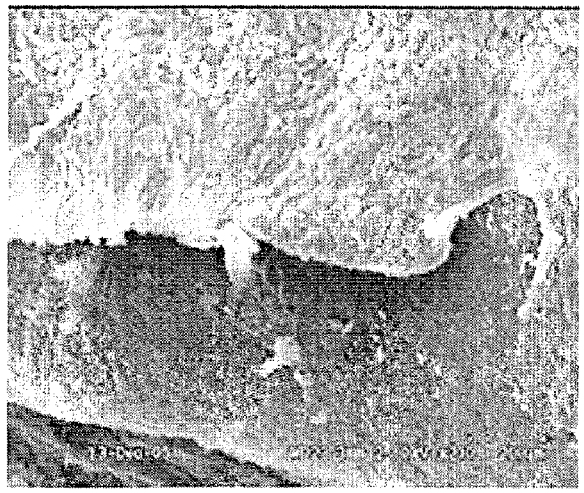
FIG. 1. SEM images of acellular nerves in cross section. The untreated nerve (a) is dense with no apparent porosity. Such a bioscaffold is difficult to seed with cells. Host cells also have difficulty infiltrating this structure. Nerves treated with 1% (b) and 5% (c) peracetic acid at 37° C. for 24 hours show graded levels of porosity. Nerve treated with 10% peracetic acid (d) shows large pores, but has lost mechanical integrity.
Figure 1:
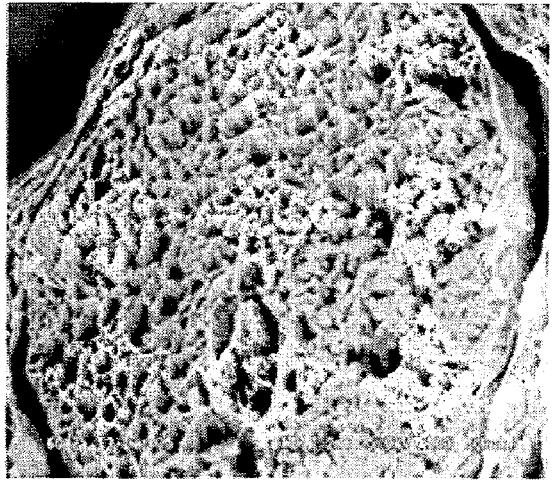
Figure 1:
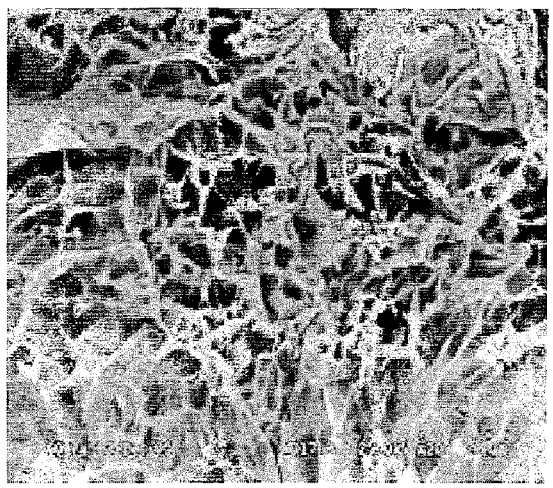
Figure 1:
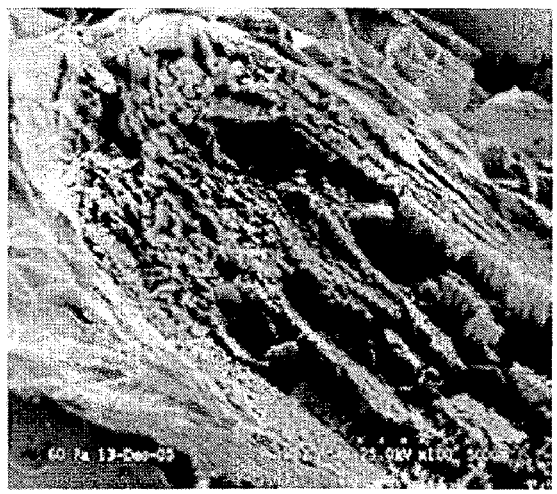

Disclosed herein are structural modifications of bioscaffolds via mechanical processes and/or chemical treatments. An architecturally-optimized scaffold can be created that retains the majority of its original biomechanical integrity. The present scaffold may therefore be able to withstand early motion and rehabilitation better than previous scaffolds, which would allow earlier functional recovery and accelerate healing after implantation.

In preferred embodiments, improved bioscaffolds disclosed herein are: 1) derived from natural tissue and amenable to host-cell mediated remodeling in vivo, 2) decellularized to minimize inflammatory potential and host immune response, 3) biocompatible, 4) modified to allow seeding, infiltration, and attachment of the patient's own cells prior to or after implantation, 5) have optimum biomechanical integrity to withstand rehabilitation until complete remodeling has occurred, and 6) possess decreased microbial load and are expected to be sterile after processing. These scaffolds promote rapid remodeling, increased strength, improved healing, and early rehabilitation and return to function after implantation. In addition, the availability of these scaffolds eliminates the donor site morbidity, increased surgical time, and poor function associated with autologous tissue harvest.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

The disclosures of all United States patent references cited herein are hereby incorporated by reference herein in their entirety.

"Bioscaffolds" or "scaffolds" as used herein refer to a substrate on which cells can grow. In preferred embodiments, the bioscaffolds are derived from natural tissues. These scaffolds are useful in both the medical and research settings. For example, the bioscaffolds disclosed herein may be used in cardiovascular tissue engineering, nerve tissue engineering, musculoskeletal tissue engineering, etc., and/or may be used in 3-D cell culture systems and bioreactor systems.

"Natural tissues" are tissues that are normally found in an animal without human manipulation. Tissues that may be used to carry out the present invention may be from any suitable animal source, including human, other mammalian (e.g., cat, dog, pig, cow, sheep, horse, monkey), avian (e.g., chicken, turkey, duck, goose, etc.), reptile, amphibian, etc. Tissues may be of any suitable type, including but not limited to: blood vessel (e.g., vein, artery) tendon, ligament, fascia, skeletal muscle, smooth muscle (e.g., bladder), cardiac muscle or heart, small intestine, large intestine, kidney, liver, pancreas, nerve (including peripheral nerve), skin, cartilage, meniscus, intervertebral discs, and bone.

More dense tissues (e.g., tissues that bear/transmit/absorb mechanical load as their primary function such as tendon, ligament, bone, meniscus, and intervertebral discs), such as the human Achilles tendon, which is commonly used for ligament reconstruction, may not decellularize to the same extent as less dense tissues. However, we have shown that the same techniques taught herein have proven successful in such dense tissues.

"Subjects" as used herein are preferably human, but also includes other mammals (e.g., cat, dog, pig, cow, sheep, horse, monkey), birds (e.g., chicken, turkey, duck, goose, etc.), reptiles, amphibians, etc.

"Grafting" as used herein refers to the placement of a biocompatible substrate, such as a bioscaffold, into a subject, with or without prior seeding and/or infiltration of cells. Similarly, "transplanting" refers to the taking of a whole or partial organ from one subject and placing it into another, or from one site to another site of the same subject. Cells can be autogeneic (i.e., from the subject to be treated), isogeneic (i.e., a genetically identical but different subject, e.g., from an identical twin), allogeneic (i.e., from a non-genetically identical member of the same species) and/or xenogeneic (i.e., from a member of a different species). Cells may be obtained from a donor (either living or cadaveric) or derived from an established cell line. To obtain cells from a donor (e.g., a potential recipient of a bioscaffold graft), standard biopsy techniques known in the art may be employed. Representative techniques are described, for example, in U.S. Pat. No. 6,536,567.

Bioscaffolds of some embodiments can be grafted with or without prior seeding with cells. The bioscaffolds of some embodiments an also be used for tissue regrafting as described in U.S. Pat. No. 7,108,721 to Huckle et al. The bioscaffolds of some embodiments may also be used in a bioreactor system, such as that described in U.S. Pat. Nos. 6,562,616 to Toner et al.; 5,459,069 to Palsson et al.; and 4,937,196 to Wrasidlo et al.

In some embodiments of the invention, the cells employed have been genetically manipulated by the introduction of exogenous genetic sequences or the inactivation or modification of endogenous sequences. For example, genes may be introduced to cause the cells to make proteins that are otherwise lacking in the host. Production of scarce but desirable proteins (in the context of certain tissues) may be enhanced, e.g., nerve growth factor (NGF) in nerve tissues.

Proteins (such as growth factors) or other additives (such as antibiotics, anti-inflammatories, and modulators of the immune response) may also be added to the cell and/or bioscaffold preparations at any time. Also, various treatments may be applied to enhance adherence of cells to the substrate and/or to each other. Appropriate treatments are described, for example, in U.S. Pat. No. 5,613,982. Such treatments include the application of various proteins, e.g., growth factors or extracellular matrix proteins to the bioscaffold substrate or to the growing construct. For example, collagen, elastin, fibronectin, laminin, or proteoglycans may be applied to the bioscaffold. The bioscaffold can be impregnated with growth factors such as nerve growth factor (NGF), aFGF, bFGF, PDGF, TGFβ, VEGF, GDF-5/6/7, BMP-1/2/3/4/5/6/7/13/12/14, IGF-1, etc., or these agents may be provided in the culture medium.

In some embodiments, grafting or transplanting may be carried out in order to repair, reconstruct, regenerate, replace, etc., various tissues, especially in applications where sufficient allograft or autograft tissue may not be available, such as tumor, trauma, infection and congenital/developmental deficiencies and diseases. It should be understood by those skilled in the art that scaffolds derived from one tissue may be used to repair or reconstruct damaged tissue of another type. For example, the tendon bioscaffold can be used for tendon reconstruction, but it is also useful in ligament reconstruction.

In some embodiments, examples of tissues that can be repaired, reconstructed, regenerated, replaced, etc., with the bioscaffolds disclosed herein include, but are not limited to, the following (inclusive of all tendons and ligaments associated with, crossing, originating or inserting).

In some embodiments, blood vessel scaffolds may be used for: internal and external carotid arteries, internal/external jugular veins, coronary arteries, pulmonary arteries and veins, splenic artery and vein, hepatic artery and vein, renal artery and vein, all gastrointestinal arteries and veins including the superior mesenteric artery and celiac artery and inferior mesenteric artery, the aorta, internal and external iliac arteries, internal and external iliac veins, deep and superficial femoral arteries and veins, popliteal artery and veins, deep and superficial arteries and veins of the upper extremity and lower extremity. All vessels, veins and arteries of the human body. All of the lymphatics of the human body.

In some embodiments, nerve scaffolds may be used for: spinal cord and nerves of the central nervous system. All nerves of the peripheral nervous system.

In some embodiments, tendon scaffolds (e.g., from flexor digitorum profundus (FDP) or Achilles tendon) may be used for: Hand/wrist: extensor tendons, flexor tendons, carpal ligaments, ligaments of the wrist. Ligaments crossing the wrist joint. Ligaments of the phalanges. All tendons and ligaments associated with or crossing the hand, wrist and phalanges. Forearm: interosseous membrane and all associated tendons and ligaments associated with and crossing the elbow. Any previous application which utilized the palmaris longus tendon autograft or allograft. Elbow: lateral/medial collateral ligaments of the elbow. Extensor, pronator, supinator and flexor tendons. Ligaments crossing the elbow joint. All tendons and ligaments associated with or crossing the shoulder. Shoulder (humerus/acromion/scapula/clavicle): tendons and ligaments of the shoulder, those connected to the clavicle, acromion, scapula and humerus. Rotator cuff tendons. Biceps tendon, triceps tendon, deltoid tendon. Coracoclavicular ligament. Acromioclavicular ligament. Spine: ligaments and tendons of the spine including the anterior longitudinal ligament, posterior longitudinal ligament, ligamentum flavum, intervertebral discs. Pelvis: ligaments and tendons of the pelvis. Hip: extensor/flexor/abductor/adductor/external and internal rotator tendons of the hip. All tendon and ligaments associated with and crossing the hip joint. Thigh: flexor and extensor tendons of the thigh including those of the quadriceps and hamstring muscle groups, all tendon and ligament structures associated with the thigh. Knee: medial/lateral collateral ligaments of the knee, posterior cruciate ligament (single-bundle and double-bundle reconstruction), anterior cruciate ligament (single-bundle and double-bundle reconstruction), meniscus, posterior lateral corner structures (popliteus tendon and lateral collateral ligament), posterior medial corner (posterior oblique ligament). Injuries associated with knee dislocation. All tendon and ligament structures crossing the knee joint. Patellar tendon and quadriceps tendon. Leg: all tendons and ligaments associated with and crossing the leg and associated with the syndesmosis. Ankle: all tendons and ligaments associated with and crossing the ankle joint including but not limited to the anterior tibiofibular ligament, posterior tibiofibular ligament, deltoid ligament, calcaneofibular, Achilles tendon. Any application which previously used the extensor hallicus longus tendon or any other intrasynovial tendon of the body. Foot: All ligamentous and tendon structures associated with the foot, tarsals, metatarsals and phalanges, including pronator tendons, supinator tendons, extensor tendons and extensor tendons.

In some embodiments, cartilage scaffolds may be used for: articular surfaces of the hip, knee, shoulder, ankle and elbow and all other synovial joints normally covered by articular cartilage, as well as those composed of elastic and fibrocartilage.

In some embodiment, meniscus scaffolds may be used for: meniscus replacement. In some embodiments, bone-derived scaffolds may be used for: all bony structures in the human body, including the teeth and skull.

In some embodiments, intervertebral disc scaffolds may be used for: intervertebral discs, joints such as the glenoid, acromioclavicular.

Non-orthopedic applications for the bioscaffolds disclosed herein include: obstetrical and gynecological, neurosurgical, cardiothoracic, urological, ophthalmologic, otolaryngology applications, applications in plastic surgery and reconstruction, transplant surgery, thoracic and gastrointestinal surgery, renal and hepatic surgery, dermatologic applications.

Mechanical Treatments

Mechanical methods for modifying natural tissues to form bioscaffolds are useful in the present invention. Some tissues contain capsular outer tissue layers such that when the cells are removed, the residual extracellular matrix (ECM) of the outer tissue layers presents a barrier to infiltrating or seeded cells. In addition, this capsular layer can have a different composition that is not ideal for cell attachment. As an example, the adventitia of arteries is a particularly tough, dense tissue layer that is impervious to cell seeding, and smooth muscle cells do not readily adhere to the adventitia ECM. This layer can be physically removed, typically by gross dissection, either before or after decellularization and the medial ECM layers exposed, resulting in better cell attachment and improved access to the interstices of the bioscaffold.

"Adventitia" as used herein refers to the outermost connective tissue covering of an organ, vessel, or other tissue structure. With respect to blood vessel bioscaffolds created by removing the adventitia, the process results in a more accessible matrix and better cell adhesion.

In general, most organs possess a capsular tissue covering. This tissue not only preserves the dimensional integrity of the organ, but also compartmentalizes organ systems and prevents adhesions between tissues. Inclusion of these capsular structures during preparation may lead to inefficient cell seeding of the resulting scaffold. Many types of scaffolds may benefit from the mechanical removal of these outer tissue layers including heart, kidney, liver, tendon, ligament, nerve and cartilage.

Chemical Treatments

Chemical treatments for modifying natural tissues to form bioscaffolds are useful in the present invention. The chemical treatments can be closely controlled so as to increase the pore size in the scaffolds and remove extraneous ECM materials, creating space for infiltrating cells. Increasing the porosity of bioscaffolds is beneficial for many tissue and organ types, particularly for dense tissues such as muscle, tendon, ligament, nerve and cartilage. Virtually any type of bioscaffold may benefit from structural modification by such chemical treatment, so long as it is balanced with the preservation of the minimum mechanical requirements for the intended application, and with the retention of beneficial ECM molecules such as cell adhesion promoters and growth factors. In preferred embodiments, the chemical treatments are performed with oxidants, which dissolve extraneous ECM.

The "extracellular matrix" or "ECM" or "interstitial structure" as used herein is any part of a tissue that is not a part of any cell. The ECM is the defining feature of connective tissue. In animals, the ECM is comprised primarily of collagen. The ECM also contains various proteins, including a wide range of cellular growth factors.

The increase in pore size and porosity improves initial cell seeding and reduces remodeling time. Removal of DNA and other cell matter from the bioscaffolds serves to reduce immunogenic foreign body reaction of the recipient subject. Though not all of the DNA must be removed, the more severe the foreign body reaction, the more likely the bioscaffold is to fibrose. Therefore, in preferred embodiments, DNA is removed such that only a mild or moderate transient foreign body reaction is instigated by grafting or transplanting the prepared bioscaffolds. By increasing pore size and porosity and decreasing cellular content in the bioscaffold, cellular in-growth can be enhanced and immunologic response can be reduced.

"Oxidants" that may be used to carry out the present invention are found, for example, in U.S. Pat. Nos. 7,029,508; 7,008,593; and 7,008,545. Oxidants may be per compounds or peroxy compounds such as a percarboxylic acid (performic acid, peracetic acid, perpropionic acid, perbenzoic acid, etc.), persulfate, perphosphate, periodate, etc.; peroxy compounds such as alkali and alkaline earth perborate salts, alkali and alkaline earth percarbonate salts, alkali and alkaline earth persulfate salts, hydrogen peroxide, percarboxylic acid and peracetic acid, hypochlorous acid or alkali and alkaline earth hypochlorite salts; etc.; hydroxylamines, ozone, etc., and combinations of the foregoing. The oxidant may comprise one or more of the foregoing in an aqueous solution in, for example, an amount from about 0.01% to about 50% by weight. In preferred embodiments, the oxidant comprises from about 3% to about 30% by weight.

As used herein, "increasing the pore size and porosity" refers to the controlled dissolving of the interstitial structure of the bioscaffold in order to create an average pore size and porosity ideal for efficient cellular infiltration. "Pore size" refers to the two-dimensional measurement of empty or void space present in a tissue, while porosity refers to the three-dimensional measurement of empty space or void volume per total volume. As those skilled in the art will appreciate, the ideal pore size and porosity will vary from tissue to tissue. It will also be understood that the treatments disclosed herein that increase the average pore size in the bioscaffolds disclosed herein also have the effect of increasing the porosity of the tissue.

In some embodiments, average pore sizes are large enough to accommodate an intact cell. For example, in some embodiments the resulting pore sizes are greater than 1 micron, and more preferably greater than 50 microns. In other embodiments, the pore size may be 100 microns or more. In some embodiments, the ideal pore size of scaffolds developed using the processes described herein on bone tissue is from 400-1000 microns. In some embodiments, the ideal pore size of ligament, tendon, and meniscus tissues is from 100-1000 microns. In preferred embodiments, the average pore size is increased by approximately 3 times the cell diameter of the cell intended to be seeded into the bioscaffold. Cells that can be seeded into the bioscaffold include stem cells (pluripotent and/or multipotent), adipose cells, tendon cells, chondrocyte cells, skeletal muscle cells, osteocyte cells, etc., without limitation (See, e.g., U.S. Pat. Nos. 6,808,704 to Lanza et al.; 6,132,463 to Lee et al.; and U.S. Patent Application Publication No. 2005/0124003 to Atala et al.). The ideal pore size in this preferred embodiment is therefore three times the average diameter of the cell selected to be seeded. In some embodiments, the average pore size is approximately three times a cell diameter of 1 to 30, 40, or 50 or more microns (i.e., 3 to 60, 80, or 100 or more microns).

The ideal pore size may also be represented as a percentage of the average pore size of the tissue before the controlled dissolving of the interstitial structure. In some embodiments, the average pore size is increased by 20, 30, 40, or 50%. In other embodiments, the average pore size is increased by 60, 70, 80, 90, or 100% or more. In other embodiments, the average pore size is increased by 150, 200, 250, 300, or 350% or more. However, the overall structural integrity necessary for the intended application must be considered when selecting for the ideal resultant pore size.

In some embodiments, production of bioscaffolds is conducted by first decellularizing the tissue of interest, for example, by the following procedure:

1. Pre-treat the tissue with deionized (DI) water or other hypotonic solution to disrupt the cells;
2. Optionally, treat the disrupted tissue with an enzyme such as trypsin to break down cell adhesions;
3. Treat the tissue with detergent solution such as 0.5% Triton X-100 (a nonionic surfactant) in ammonium hydroxide;
4. Optionally, but preferably, wash residual reagents out of the bioscaffold with repeated washes of DI water.

In some embodiments, the decellularizing step may be carried out as described in U.S. Pat. No. 6,753,181 to Atala, by: mechanically agitating tissue (e.g., a complete organ or a portion thereof) in membrane stripping fluid to disrupt cell membranes while maintaining the interstitial structure of the tissue; treating the isolated tissue in a solubilizing fluid at a concentration effective to extract cellular material from the tissue while maintaining the interstitial structure of the tissue; and optionally washing the isolated tissue in a washing fluid to remove cellular debris while maintaining the interstitial structure of the tissue until the isolated tissue is substantially free of cellular material, to thereby produce a decellularized tissue scaffold (in some embodiments washing may optionally be deferred until after the oxidizing step).

The step of mechanically agitating the tissue may comprise placing the tissue in a stirring vessel having a paddle that rotates at a speed ranging from about 50 revolutions per minute (rpm) to about 150 rpm. The step of mechanically agitating the isolated tissue may occur in a non-detergent membrane stripping fluid (e.g., distilled water, physiological buffer or culture medium). The step of treating the isolated tissue in the solubilizing fluid may also occur in a stirring vessel. The treating step may comprise using a solubilizing fluid that is an alkaline solution having a detergent. The treating step may comprise treating the isolated tissue in an alkaline solution (for example, a solution selected from the group consisting of sulphates, acetates, carbonates, bicarbonates and hydroxides, and a detergent selected from the group consisting of Triton X-100, Triton N-101, Triton X-114, Triton X-405, Triton X-705, and Triton DF-16, monolaurate (Tween 20), monopalmitate (Tween 40), monooleate (Tween 80), polyoxethylene-23-lauryl ether (Brij 35), polyoxyethylene ether W-1 (Polyox), sodium cholate, deoxycholates, CHAPS, saponin, n-Decyl β-D-glucopuranoside, n-heptyl β-D glucopyranoside, n-Octyl α.-D-glucopyranoside and Nonidet P-40).

The examples of decellularization techniques provided above are not intended to be limiting, and the invention encompasses the use of essentially any decellularization technique that removes a substantial fraction of the cells while leaving the interstitial structure substantially intact. Alternatively, the decellularization may be combined with the chemical modifications as described below to remove extraneous ECM materials and increase the average pore size.

It will be appreciated by those skilled in the art that certain techniques will be preferred for particular tissue engineered constructs or native tissues, depending upon the properties of these constructs or tissues. An appropriate decellularization technique may be selected and parameters such as temperature and time may be optimized in order to achieve a desired degree of decellularization. In some embodiments of the invention the decellularization process removes at least 50% of the cells. In some embodiments of the invention the decellularization process removes at least 60%, at least 70%, or at least 80% of the cells. In some embodiments of the invention at least 90%, at least 95%, or substantially all of the cells are removed. As described above, there may be a tradeoff between the two goals of achieving a high degree of decellularization and preserving the structure and properties of the extracellular matrix. Thus it is not necessarily preferred to achieve maximal possible decellularization if doing so results in unacceptable damage to the extracellular matrix. The optimum degree of decellularization may depend upon the properties of the construct and the use for which it is intended.

In preferred embodiments, after decellularization the dense bioscaffold is treated with an oxidant solution to effectively remove extraneous ECM materials and increase the average pore size. Any type of water-soluble oxidant can be used. Preferred oxidants include hydrogen peroxide and peracetic acid. The decellularization and oxidizing steps may also be combined, or the oxidizing step may be performed before the decellularization step.

Typical oxidant concentrations range from 1, 1.5, 2 or 3 to 30, 32, or 34%, and up to 50% (w/v) and will vary depending on the starting density of the tissue and desired degree of porosity. A preferred concentration for nerve tissue is approximately 5% and for tendon is approximately 1.5%, for example. After oxidation, residual chemicals may be removed by repeated washes with DI water and conditioned in a final step by incubation with phosphate buffered saline (PBS). The scaffold may also be freeze-dried and sterilized (e.g., by cold gas) prior to use.

For chemical modification, a batch process can be used to modify large numbers of bioscaffolds at one time. The increase in porosity can be controlled as in any kinetic process by changing oxidant concentration, time, and temperature. Similar to the decellularization step discussed above, there may be a tradeoff between the two goals of achieving adequate porosity and preserving the structure and properties of the extracellular matrix. Thus, it is not necessarily preferred to achieve maximal possible porosity if doing so results in unacceptable damage to the extracellular matrix. The optimum degree of porosity may depend upon the properties of the construct and the use for which it is intended.

In preferred embodiments, the oxidant is added sequentially or simultaneously with the detergent. Simultaneously is close enough in time that combining the two steps (oxidant and detergent) will increase removal of cellular material and DNA. For example, oxidation occurs in conjunction with decellularization and cellular material is only minimally removed from the musculoskeletal dense tissues if the reagents are used separately. In some embodiments, using oxidant and detergent simultaneously increases the removal of DNA and minimizes residual DNA.

The optimized bioscaffolds disclosed herein minimize immunogenic and inflammatory potential of the implanted scaffold in the host after implantation and maximize host cell infiltration into the scaffold in vivo or in vitro. These disclosed modifications will decrease the time necessary for cellular repopulation in vivo or cell seeding in vitro and reduce the time necessary for remodeling of collagen fibrils, which subsequently improves the biomechanical integration of the scaffolds in vivo. All of these factors have been implicated in the poor incorporation of current grafts used by others in reconstruction of tissues. The removal of extraneous cellular material greatly reduces the potential for inflammation and disease transmission upon implantation of the scaffold.

The present invention is explained in greater detail in the following non-limiting Examples.

EXAMPLES

Example 1

Nerve Scaffolds

Sciatic nerves were harvested from white New Zealand rabbits. The tissue was placed in deionized (DI) water and shaken at 4° C. for 48 hours to break open the cells. Cell fragments were removed by extraction at 4° C. with 0.5% Triton X-100 in 0.05% sodium hydroxide solution for 48 hours. Residual reagents were removed by shaking in DI water at 37° C. for 96 hours. Efficient removal of the cellular material was confirmed by histological, microscopic, and residual DNA analyses. To increase the porosity and interconnectivity, the acellular nerves were treated at 37° C. for 24 hours with peracetic acid at concentrations of 1, 5, and 10 w/v %. Residual oxidant was removed by repeated extractions with DI water. Finally, the bioscaffolds were freeze dried prior to analysis by scanning electron microscopy (SEM).

The SEM results are summarized in FIG. 1. These data demonstrate the efficacy of oxidant treatment on peripheral nerve bioscaffolds. In cross section, the untreated nerve is dense with no apparent porosity. Treatment with peracetic acid concentration as low as 1% has a dramatic effect on the degree of resulting porosity. However, extensive oxidation can result in loss of mechanical integrity as is shown in FIG.

1d. Clearly, the kinetic parameters can be adjusted to obtain optimal pore size and interconnectivity without appreciable loss of mechanical strength.

Example 2

Tendon Scaffolds

The feet of 56 day old Leghorn chickens were provided by Wayne Farms (Dobson, N.C.), placed on ice immediately after receipt, and stored at 4° C. until harvest. The feet were cleaned and disinfected using aseptic techniques. The flexor digitorum profundus (FDP) tendon from the long digit was removed and placed into a sterile, 15 ml conical tube (Becton Dickinson, Bedford, Mass.).

A. Preparation of Decellularized/Oxidized FDP Tendon Scaffolds. Immediately after harvest, FDP tendons were transferred under aseptic conditions from 15 ml conical tubes to individual clean, autoclaved, 100 ml glass, screw-top bottles (Gibco, Grand Island, N.Y.). 100 ml of DNase-free/RNase-free, distilled water (Gibco) was added to each sample. The bottle was placed onto a rotating shaker (Barnstead MaxQ400, Dubuque, Iowa) at 200 rpm, 37° C., for 24 hours. After 24 hours, the water was discarded and the cycle was repeated. At the conclusion of the second cycle, the water was discarded and 100 ml of 0.05% trypsin (Sigma, St. Louis, Mo.), 4.0 mM sodium bicarbonate (Sigma), and 0.5 mM tetrasodium EDTA (Sigma), prepared in Hank's Balanced Salt Solution (Gibco) was added. The sample was placed onto the rotating shaker at 200 rpm, 37° C. for 1 hour. At the end of the cycle, the trypsin solution was discarded and 100 ml of Dulbecco's Modified Eagle's Medium (DMEM) high-glucose (Gibco) containing 10% fetal bovine serum (FBS) (Valley Labs, Winchester, Va.) and 100 I.U./ml Penicillin, 100 µg/ml Streptomycin, 0.25 µg/ml Amphotercin B (Gibco) was added in order to halt trypsin digestion of the sample. The sample was placed back onto the rotary shaker at 200 rpm, 37° C., for 24 hours. After 24 hours, the DMEM-FBS solution was discarded and 100 ml of the DNase-free/RNase-free distilled water was added and the sample was placed onto the rotary shaker at 200 rpm, 37° C. for 24 hours. The water wash was discarded and 100 ml of 1.5% peracetic acid (Sigma) solution with 1.5% Triton X-100 (Sigma) in distilled, deionized water (diH2O) was added and the sample placed onto the rotary shaker at 200 rpm, 37° C. for 4 hours. The solution was discarded and two 100 ml washes with diH2O were performed, each for 12 hours at 37° C. and 200 rpm on the rotary shaker. At the end of the second wash, the sample was removed and placed into a clean, sterile 15 ml conical tube and frozen for 24 hours at –80° C. The sample was then freeze-dried (Labconco, Freeze Dry System, Kansas City, Mo.) for 24 hours before being returned to the freezer and stored at –80° C. until further use.

B. Histologic Analysis of Fresh-Frozen FDP Tendons and Decellularized/Oxidized FDP Tendon Scaffolds. Mid-substance portions of fresh-frozen FDP tendon and decellularized/oxidized FDP tendon scaffold were placed in 10% phosphate-buffered formalin at room temperature for 4 hours. The tendons then were processed for histology, embedded in paraffin, and microtomed to obtain 5.0 µm thick, longitudinal sections. The sections were mounted on slides and stained using hematoxylin and eosin (H&E, Sigma) as well as 4,6-diamidino-2-phenylindole (DAPI) (Vector, Burlingame, Calif.) to identify cellular and nuclear components, respectively. Representative light (H&E) and fluorescence (DAPI) micrographs were taken at 100× magnification.

Figure 2:
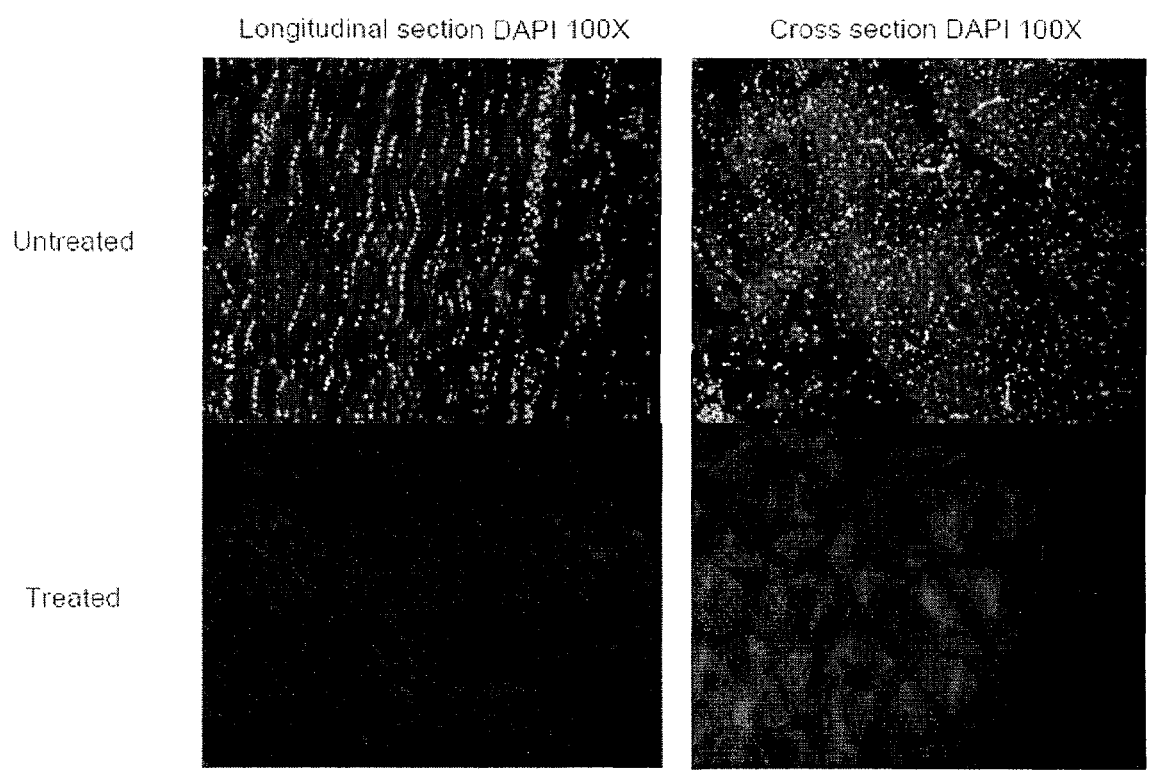
FIG. 2. DAPI staining of both longitudinal and cross sections show the dramatic reduction in cellular density of chicken tendon treated with an oxidant-detergent solution.

Abundant cellular material, specifically nuclear material, was evident after H&E and 4',6-diamidino-2-phenylindole (DAPI) staining of longitudinal sections of fresh-frozen Leghorn chicken FDP tendon prior to decellularization/oxidation (FIG. 2). The low or absent porosity was observed in H&E stained sections of the FDP tendons. After decellularization and oxidation, no nuclear material was evident via H&E staining. DAPI staining revealed the presence of DNA and RNA within the decellularized/oxidized tendon scaffolds (FIG. 2). However, this material was neither organized, nor condensed in appearance as seen in the untreated tendons. An increase in intra-fascicular and inter-fascicular space after treatment was also observed via H&E staining.

Figure 3:
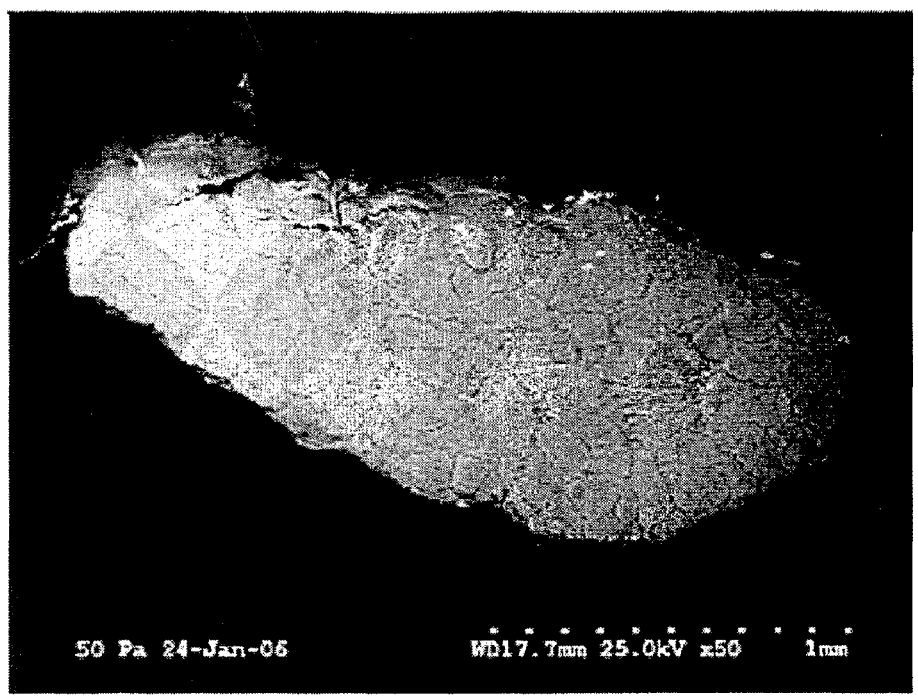
FIG. 3. Flexor digitorum profundus (FDP) and the decellularized/oxidized FDP tendon scaffold, scanning electron microscopy (SEM), 50×, cross section. The microarchitecture of the untreated tendon is very dense compared to the tendon following treatment with an oxidant-detergent solution, which is characterized by an increase in pore size and porosity.
Figure 3:

C. Scanning Electron Microscopy of Fresh-Frozen FDP Tendons and Decellularized/Oxidized FDP Tendon Scaffolds. Scanning electron microscopy confirmed the dense micro-architecture observed in histologic sections of fresh-frozen FDP tendon, as well as an increase in pore size and porosity following treatment (FIG. 3). Scanning electron microscopy was performed on fresh-frozen FDP tendons and decellularized/oxidized FDP tendon scaffolds. Specimens of the fresh-frozen FDP tendon and the FDP tendon scaffold were removed directly from storage at –80° C., equilibrated in DNase-free/RNase-free water at 37° C. for 30 minutes, patted dry and mounted for analysis. Cross-sectional electronmicrographs were obtained at 25.0 kV, 50 Pa, 50× magnification using a Hitachi S-2600 Scanning Electron Microscope (Hitachi High Technologies America, Pleasanton, Calif.).

D. Determination of DNA Content in Fresh-Frozen FDP Tendons and Decellularized/Oxidized FDP Tendon Scaffolds. Fresh-frozen FDP tendons (n=16) stored at –80° C. for 24 hours were lyophilized for 24 hours. Samples then were weighed and placed into sterile 1.5 ml micro-centrifuge tubes. This process was repeated for the decellularized/oxidized FDP tendon scaffolds which previously had been freeze dried as part of their preparation process (n=8). Total DNA was then isolated from this tissue using a commercially available kit (DNeasy™, Qiagen, Valencia, Calif.). The DNA concentration in the resulting volume was used to calculate total DNA content at $\lambda=280$ nm using a spectrophotometer (Thermo Spectronic, Biomate 3, Rochester, N.Y.), which was then normalized using the initial dry weight of the sample.

Figure 4:
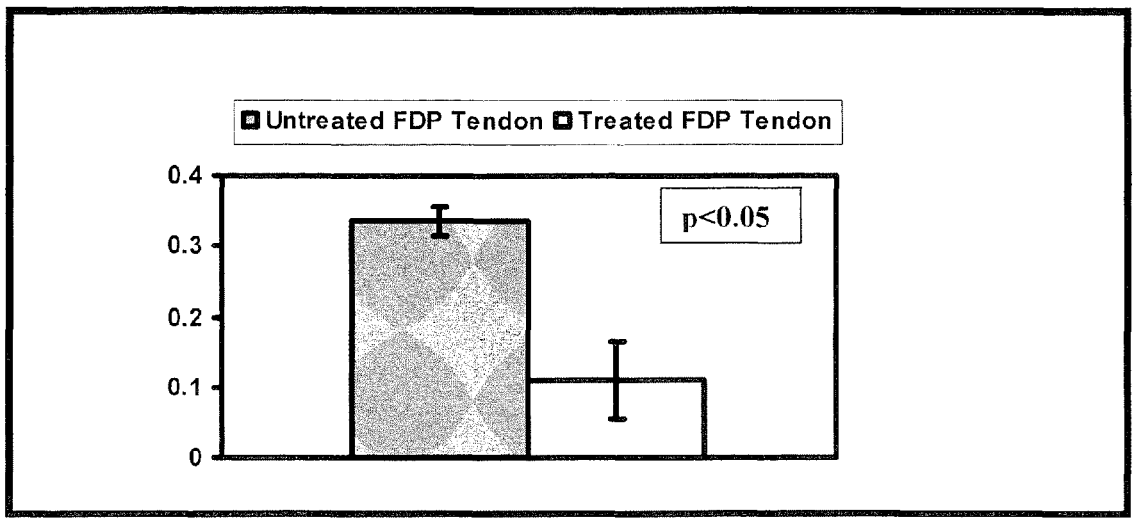
FIG. 4. DNA Content. Fresh-frozen FDP tendon ("untreated") and decellularized/oxidized FDP tendon scaffold ("treated") dry weight DNA content determined using the DNeasy™ assay. There is a significant decrease in the DNA content of the decellularized/oxidized FDP tendon scaffold (67%, $p<0.05$, µg DNA/mg tissue dry weight+/−SEM, two-tailed, Student's t-test with unequal variances) when compared to fresh-frozen FDP tendon, indicating that nuclear material, and therefore cellular material, has been removed.

DNA content of the FDP tendon scaffolds was significantly decreased by 67.14% (0.1102+/–0.0542 µg DNA/mg tissue dry weight, n=8) after treatment when compared to untreated (i.e. fresh-frozen) FDP tendons (0.3354+/–0.0200 µg DNA/mg tissue dry weight, n=16), p<0.001 (FIG. 4).

E. In Vitro Biocompatibility of Decellularized/Oxidized FDP Tendon Scaffolds: Direct Contact Method. Representative specimens (approximately 0.04 cm$^3$ portion/well) of the decellularized/oxidized chicken FDP tendon scaffold (n=10) were placed in the center of sub-confluent murine NIH 3T3 cell monolayers in 96-well plates (Becton Dickinson), which covered one-tenth of the surface area, according to established standards (Pariente et al. (2001) *J Biomed Mater Res* 55:33-39). The same procedure was followed using latex (Ansell, Massillon, Ohio) as a negative control (n=10). Cells not exposed to any foreign material served as a positive control (n=10). The cell-material contact was maintained for 72 hours at 37° C. and 5% $CO_2$.

At the end of the incubation, the test materials were removed and two separate assays were performed to measure metabolic activity (MTS® solution) and cell viability (Neutral Red). Briefly, 40 µL of MTS® solution (Promega, Madison, Wis.) was added into each well. After a 3 hour incubation at 37° C., the absorbance of the solution was measured at 490 nm using a 96-well plate spectrophotometer (Biotek, ELX800, Winoski, Vt.). The absorbance obtained was directly proportional to the metabolic activity of the cell populations and inversely proportional to the toxicity of the material.

For the cell viability assay, the media was removed and the cell layers rinsed with 200 μL of cold PBS. 100 μL of neutral red solution (Sigma, 0.005% weight/volume in culture medium) was then added into each well. After a 3 hour incubation period at 37° C., the neutral red solution was removed and dye extraction performed by adding 100 μL of 1% (volume/volume) acetic acid in 50% (volume/volume) ethanol solution into each well. The plates were agitated on a platform shaker (Barnstead) for 5 minutes. Absorbance was measured at $\lambda$=540 nm using the 96-well plate spectrophotometer noted above. The absorbance obtained was directly proportional to the viability of the cell populations and inversely proportional to the toxicity of the material. The negative control (cells exposed to latex) for both assays was considered satisfactory if the observed absorbance for both assays was <10% of that observed for the positive control (cells exposed to media alone).

Figure 5A:
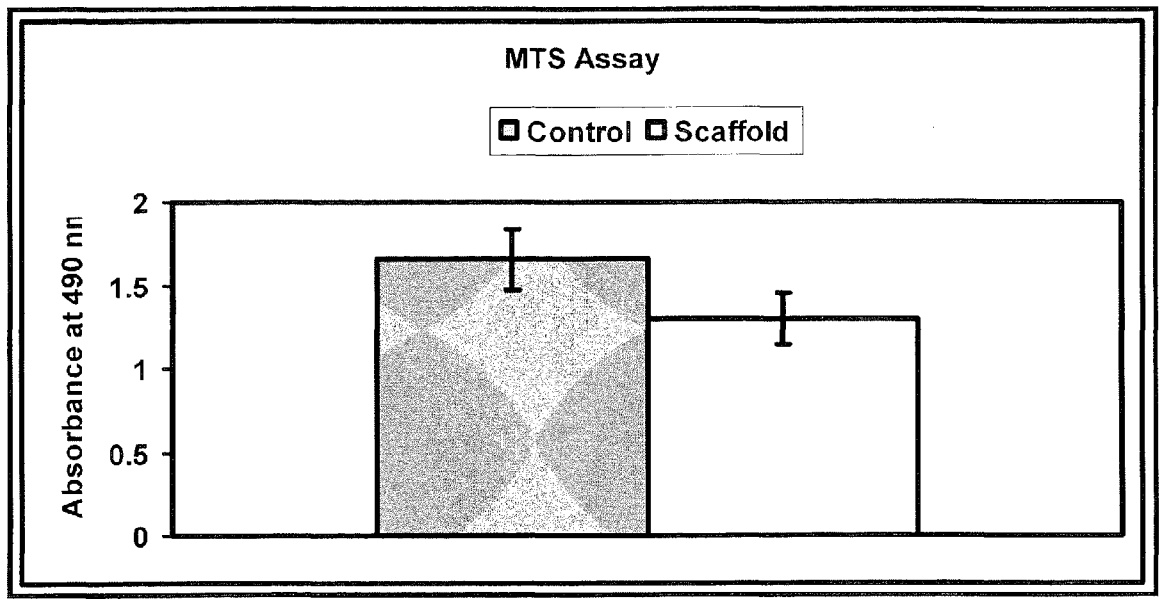
FIGS. 5A-5B.
Figure 5B:
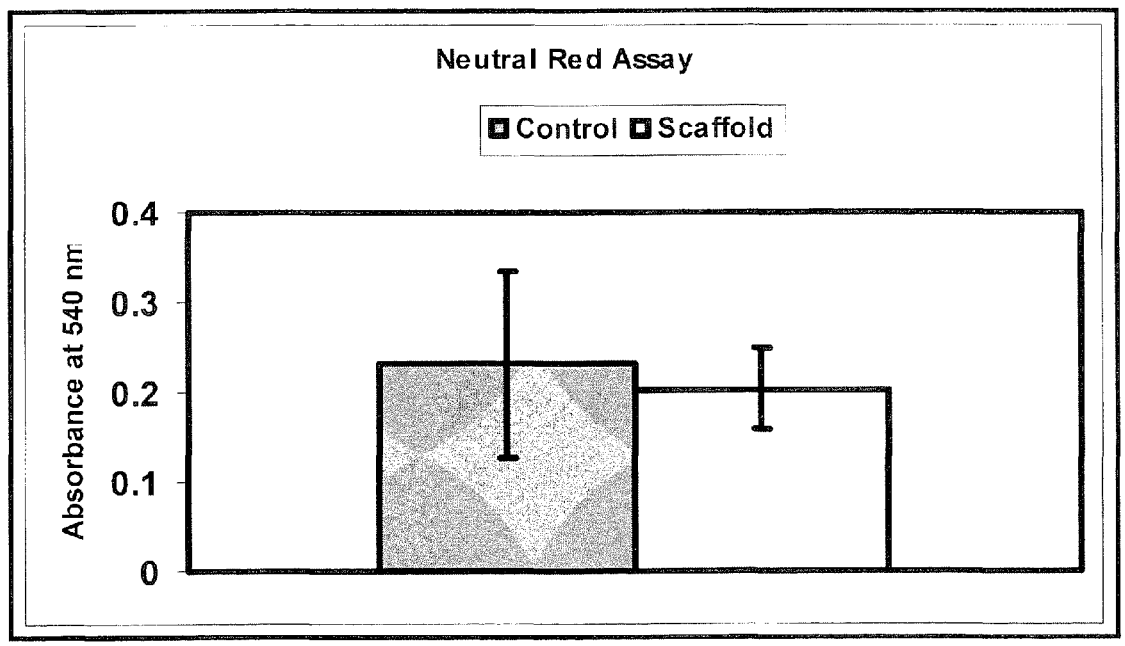

Mitochondrial activity determined using the MTS® assay (absorbance at $\lambda$=490 nm) for NIH 3T3 cells exposed to the decellularized/oxidized chicken FDP scaffold was 79% (1.300+/−0.049, n=10) of that observed for cells exposed to media only (1.654+/−0.057, n=10) and was statistically significant (p<0.001, FIG. 5A). However, cell viability determined using the Neutral Red assay (absorbance at $\lambda$=540 nm) for NIH 3T3 cells exposed to the decellularized/oxidized chicken FDP scaffold was 88% (0.204+/−0.014, n=10) of that observed for NIH 3T3 cells exposed to media alone (0.231+/−0.033, n=10, positive control), a difference which was not statistically significant (FIG. 5B). The decellularized/oxidized scaffold and positive control (cells only) differed significantly (p<0.001) from the values obtained for a known cytotoxic material (latex, negative control, n=10) in both assays. The absorbance observed for the negative control was also <10% of the absorbance observed for positive controls in each assay.

F. Tensile Testing. Fresh-frozen FDP tendons (n=6) and decellularized and oxidized FDP tendon scaffolds (n=10) were removed from storage at −80° C. and allowed to equilibrate in sterile Dulbecco's phosphate buffered saline at 37° C. for 30 minutes. Tendons then cut into "dogbone" specimens using a custom made punch (Freeman, Fremont, Ohio), their ends wrapped with saline-soaked gauze, and placed into custom made grips on an uniaxial load frame (Instron 5544, Needham, Mass.) for tensile testing. Samples were measured prior to testing with digital calipers to determine cross-sectional area ($mm^2$) and length (mm). Tendons were pre-loaded to 0.1N, and then pre-conditioned 10 times to 0.1 mm extension prior to being loaded to failure at a rate of 10 mm/minute. Ultimate tensile stress at break (MPa) and elastic modulus (MPa) then were determined using the stress-strain curve obtained from the instrument.

Figure 6A:
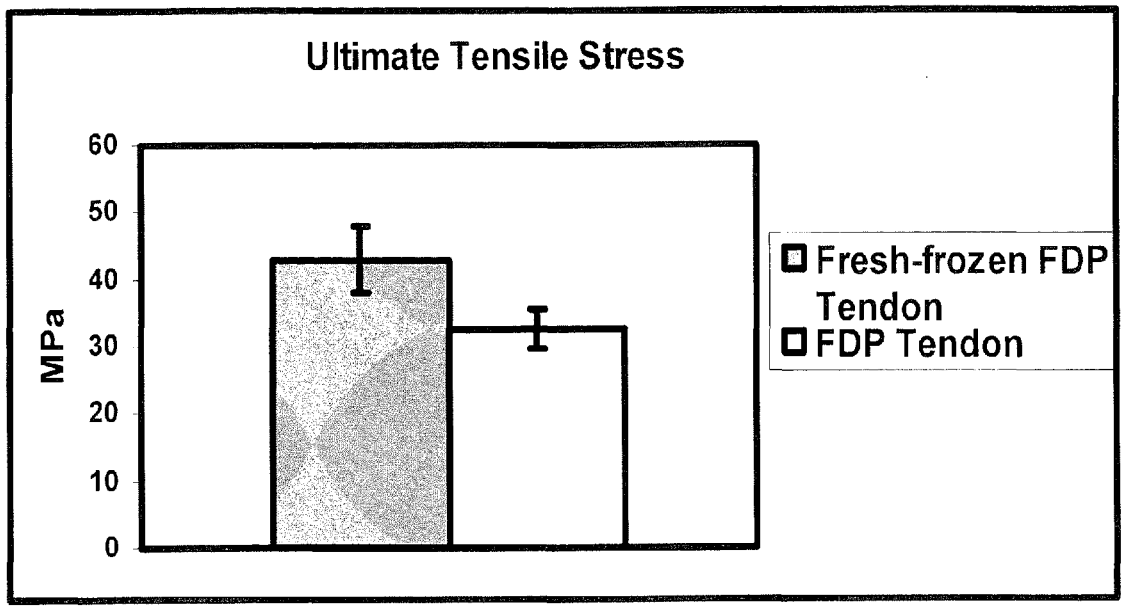
FIGS. 6A-6B. Tensile Testing: The ultimate Tensile Stress at Break (MPa) (FIG. 6A) and Modulus of Elasticity (MPa) (FIG. 6B) observed for the decellularized/oxidized FDP tendon scaffold were 76% and 78%, respectively, of the values observed for fresh-frozen FDP tendon and were not significantly weaker ($p>0.05$, MPa+/−SEM, two-tailed, Student's t-test with unequal variances).
Figure 6B:
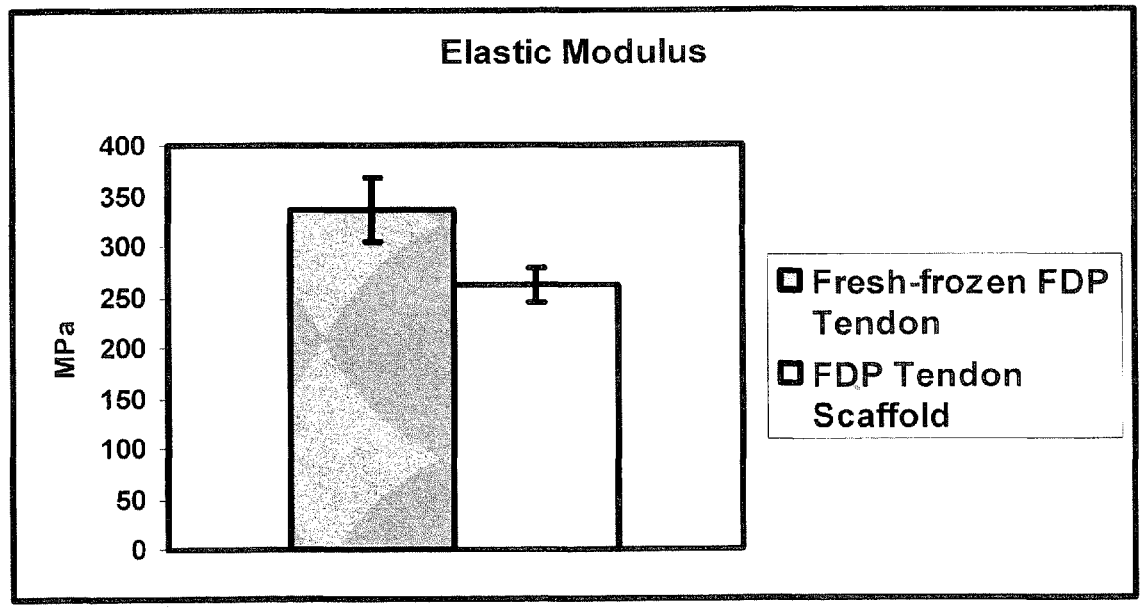

Mechanical testing of decellularized/oxidized FDP tendon scaffolds determined that the ultimate stress at break (MPa) was 76% (32.48+/−2.98 MPa, n=12) of that observed for fresh-frozen FDP tendons (42.95+/−5.04 MPa, n=8) and that the difference was not statistically significant (FIG. 6A). Similarly, elastic modulus (E) was reduced in decellularized and oxidized FDP tendons (261.12+/−17.32 MPa, n=12) to 77% of the value observed for fresh-frozen FDP tendons (335.48+/−31.92 MPa, n=6), and that the difference was not statistically significant (FIG. 6B). Only specimens that failed in the mid-substance region of the tendon and scaffold were included. Specimens that failed at the grips were excluded from calculations.

G. In Vivo Cell Infiltration and Inflammatory Response of Decellularized/Oxidized FDP Tendon Scaffolds. To assess inflammatory response and cell infiltration in vivo, scaffolds were implanted subcutaneously in 10 week-old, female CD1 mice using aseptic technique. Briefly, a 3 mm incision was made on the dorsum of the mouse and a tissue pocket created using blunt dissection with scissors. Implants (1 per mouse, n=3 per time point) of approximately 1 mm thick×2 mm×2 mm in size of decellularized/oxidized tendon scaffolds (ethylene-oxide sterilized) were placed and the wound closed with suture and wound adhesive. The implants were harvested at 3, 7, 14, and 21 days post-implantation and examined grossly and histologically (H&E).

Figure 7:
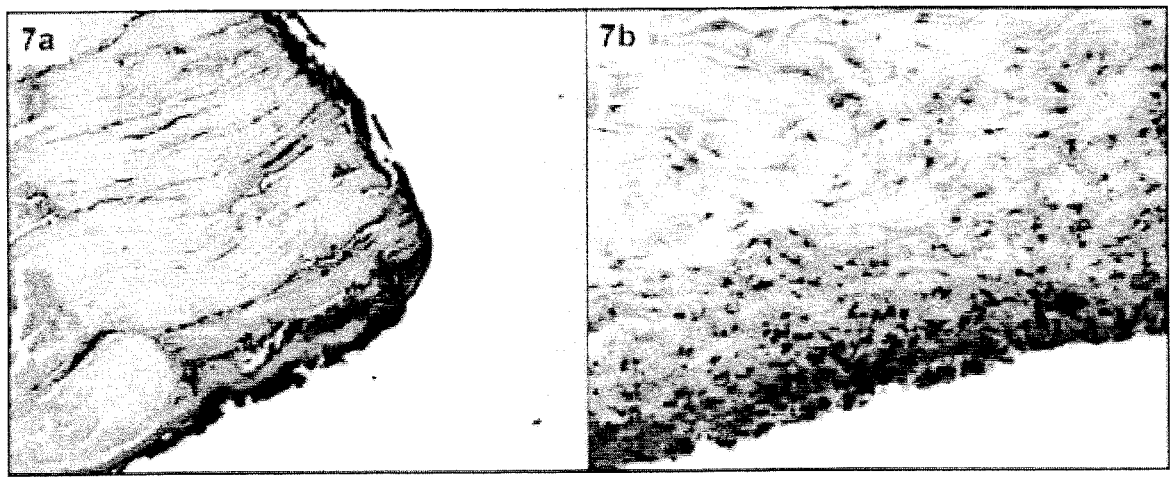
FIG. 7. Decellularized/oxidized FDP tendon scaffold 3 days after subcutaneous implantation in CD1 mice, H&E, 100×, longitudinal section: (a) Fusiform cells, consistent with fibroblasts, are visible at the periphery as well as within the scaffold matrix. Decellularized/oxidized FDP tendon scaffold 21 days after implantation, H&E, 100×, longitudinal section: (b) An increase in the number of fibroblast-like cells within the scaffold matrix is apparent after 21 days in vivo. There is no evidence of an inflammatory reaction or capsule formation in either micrograph.

Cell infiltration was observed in H&E-stained sections of explanted decellularized/oxidized FDP tendon scaffolds at 3, 7, 14 and 21 days postimplantation in immune-competent, female, 10 week-old CD1 mice. Representative light micrographs of H&E-stained longitudinal sections of explanted tendon at 3 days (FIG. 7, left panel) and 21 days (FIG. 7, right panel) post-implantation are shown. No evidence of a gross inflammatory reaction or capsule formation was observed at either time of explantation.

H. Statistical Analysis. For DNA content, MTS™, neutral red, and biomechanical analyses, samples were analyzed in replicate, averaged, a standard error of the mean (SEM) was calculated and a comparison was made between groups using a two-tailed, Student's t-test with unequal variances. Differences were considered significant at p<0.05.

I. Conclusions. Increased tendon pore size and porosity were produced using chemical oxidation resulting in a scaffold that is more likely to allow cell infiltration and repopulation. Additionally, the tissue-engineered FDP tendon scaffold is biocompatible in vitro when assessed via the MTS® and Neutral Red assays. The FDP tendon scaffolds also retained approximately 76-78% of the initial mechanical properties of fresh-frozen FDP tendons, a difference that was not statistically significant. The FDP tendon scaffolds did not exhibit any evidence of a gross inflammatory reaction at 3, 7, 14 or 21 days when implanted subcutaneously in an immunocompetent mouse. Finally, cell infiltration by fibroblast-like host cells was observed at all time points after subcutaneous implantation of FDP tendon scaffolds.

Example 3

Tendon Scaffolds

Experiments with the human Achilles tendon have produced similar results as those reported in Example 2.

A. Preparation of Decellularized/Oxidized Achilles-derived Tendon Scaffolds. Freeze-dried human Achilles tendon allografts from multiple donors were provided and stored at 25° C. until use. Freeze-dried human Achilles tendon allografts were transferred under aseptic conditions to individual clean, autoclaved, 1000 ml glass flasks. 1000 ml of DNase-free/RNase-free, distilled water (Gibco) was added to each sample. The flask was placed onto a rotating shaker (Barnstead MaxQ400, Dubuque, Iowa) at 200 rpm, 37° C., for 24 hours. After 24 hours, the water was discarded and the cycle was repeated. At the conclusion of the second cycle, the water was discarded and 500 ml of 0.05% trypsin-EDTA (Gibco) was added. The sample was placed onto the rotating shaker at 200 rpm, 37° C. for 1 hour. At the end of the cycle, the trypsin solution was discarded and 500 ml of Dulbecco's Modified Eagle's Medium (DMEM) high-glucose (Gibco) containing 10% fetal bovine serum (FBS) (Valley Labs, Winchester, Va.) and 100 I.U./ml Penicillin, 100 µg/ml Streptomycin, 0.25 µg/ml Amphotercin B (Gibco) was added in order to halt trypsin digestion of the sample. The sample was placed back onto the rotary shaker at 200 rpm, 37° C., for 24 hours. After 24 hours, the DMEM-FBS solution was discarded and 1000 ml of the DNase-free/RNase-free distilled water was added and the sample was placed onto the rotary shaker at 200 rpm, 37° C. for 24 hours. The water wash was discarded and 1000 ml of 1.5% peracetic acid (Sigma) solution with 1.5% Triton X-100 (Sigma) in distilled, deionized water (diH2O) was added and the sample placed onto the rotary shaker at 200 rpm, 37° C. for 4 hours. The solution was discarded and three 1000 ml washes with $diH_2O$ were performed, each for 12 hours at 37° C. and 200 rpm on the rotary shaker. At the end of the third wash, the sample was removed and placed into a clean, sterile freezer bag and frozen for 24 hours at −80° C. The sample was then freeze-dried (Labconco, Freeze Dry System, Kansas City, Mo.) for 48 hours before being returned to the freezer and stored at −80° C. until further use.

B. Histologic Analysis of Freeze-dried Human Achilles Tendon Allografts and Decellularized/Oxidized Freeze-dried Human Achilles Tendon Allograft-derived Scaffolds. Midsubstance portions of freeze-dried human Achilles tendon allograft and decellularized/oxidized freeze-dried human Achilles tendon allograft-derived scaffold were placed in 10% phosphate-buffered formalin at room temperature for 4 hours. The tendons then were processed for histology, embedded in paraffin, and microtomed to obtain 5.0 µm thick, longitudinal sections. The sections were mounted on slides and stained using hematoxylin and eosin (H&E, Sigma) as well as 4',6-diamidino-2-phenylindole (DAPI) (Vector, Burlingame, Calif.) to identify cellular and nuclear components, respectively. Representative light (H&E) and fluorescence (DAPI) micrographs were taken at 100× magnification.

Figure 8A:
FIGS. 8A-8B. H&E and DAPI staining of freeze-dried human Achilles tendon allograft.
Figure 8A:
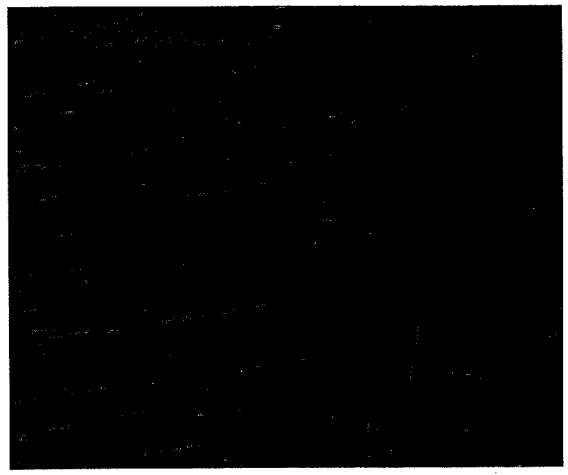
Figure 8B:
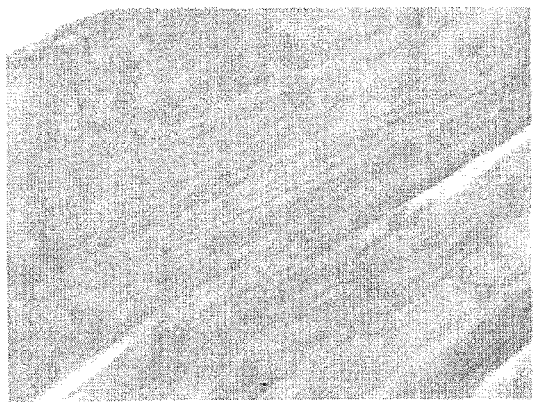
Figure 8B:
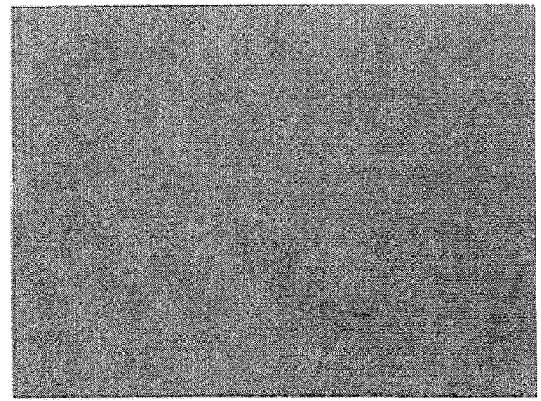

Abundant cellular material, specifically nuclear material, was evident after H&E and 4',6-diamidino-2-phenylindole (DAPI) staining of longitudinal sections of freeze-dried human Achilles tendon allograft prior to decellularization/oxidation (FIG. 8A). Minimal porosity was observed in H&E stained sections of the freeze-dried human Achilles tendon allograft. After decellularization and oxidation, no nuclear material was evident via H&E staining. DAPI staining revealed the presence of DNA and RNA within the decellularized/oxidized tendon scaffolds (FIG. 8B). However, this material was neither organized, nor condensed in appearance as seen in the untreated tendons. An increase in intra-fascicular and inter-fascicular space after treatment was also observed via H&E staining.

C. Determination of DNA Content in Decellularized/Oxidized Freeze-dried Human Achilles Tendon Allograft-derived Scaffolds and Decellularized/Oxidized Freeze-dried Human Achilles Tendon Allograft-derived Scaffolds. Freeze-dried human Achilles tendon allograft (n=10) stored at −80° C. for 24 hours were lyophilized for 24 hours. Samples then were weighed and placed into sterile 1.5 ml micro-centrifuge tubes. This process was repeated for the decellularized/oxidized tendon scaffolds which previously had been freeze dried as part of their preparation process (n=8). Total DNA was then isolated from this tissue using a commercially available kit (DNeasy™, Qiagen, Valencia, Calif.). The DNA concentration in the resulting volume was used to calculate total DNA content at $\lambda$=280 nm using a spectrophotometer (Thermo Spectronic, Biomate 3, Rochester, N.Y.), which was then normalized using the initial dry weight of the sample.

DNA content of the decellularized/oxidized freeze-dried human Achilles tendon allograft-derived scaffolds was significantly decreased by 75% (0.110+/−0.02 µg DNA/mg tissue dry weight, n=10) after treatment when compared to untreated freeze-dried human Achilles tendon allografts (0.40+/−0.14 µg DNA/mg tissue dry weight, n=10), p<0.05 (FIG. 9).

D. Transmission Electron Microscopy of Freeze-Dried Human Achilles Tendon Allografts and Decellularized/Oxidized Freeze-Dried Human Achilles Tendon Allograft-Derived Scaffolds: Ultra-Structural Modification.

Transmission electron microscopy revealed a large decrease in fibril density per unit area after treatment of the freeze-dried human Achilles tendon allograft, which represents an increase on pore size and porosity of the scaffold produced using the process described herein (FIGS. 10A and 10B).

E. In Vitro Biocompatibility of Decellularized/Oxidized Freeze-dried Human Achilles Tendon Allograft-derived Scaffolds: Direct Contact Method. Representative specimens (approximately 0.04 $cm^3$ portion/well) of the decellularized/oxidized freeze-dried human achilles tendon allograft-derived scaffolds (n=10) were placed in the center of sub-confluent murine NIH 3T3 cell monolayers in 96-well plates (Becton Dickinson), which covered one-tenth of the surface area, according to established standards (Pariente et al. (2001) *J Biomed Mater Res* 55:33-39). The same procedure was followed using latex (Ansell, Massillon, Ohio) as a negative control (n=10). Cells not exposed to any foreign material served as a positive control (n=10). The cell-material contact was maintained for 72 hours at 37° C. and 5% $CO_2$.

At the end of the incubation, the test materials were removed and two separate assays were performed to measure metabolic activity (MTS® solution) and cell viability (Neutral Red). Briefly, 40 µL of MTS solution (Promega, Madison, Wis.) was added into each well. After a 3 hour incubation at 37° C., the absorbance of the solution was measured at 490 nm using a 96-well plate spectrophotometer (Biotek, ELX800, Winoski, Vt.). The absorbance obtained was directly proportional to the metabolic activity of the cell populations and inversely proportional to the toxicity of the material.

For the cell viability assay, the media was removed and the cell layers rinsed with 200 µL of cold PBS. 100 µL of neutral red solution (Sigma, 0.005% weight/volume in culture medium) was then added into each well. After a 3 hour incubation period at 37° C., the neutral red solution was removed and dye extraction performed by adding 100 µL of 1% (volume/volume) acetic acid in 50% (volume/volume) ethanol solution into each well. The plates were agitated on a platform shaker (Barnstead) for 5 minutes. Absorbance was measured at $\lambda$=540 nm using the 96-well plate spectrophotometer noted above. The absorbance obtained was directly proportional to the viability of the cell populations and inversely proportional to the toxicity of the material. The negative control (cells exposed to latex) for both assays was considered satisfactory if the observed absorbance for both assays was <10% of that observed for the positive control (cells exposed to media alone).

Mitochondrial activity determined using the MTS assay (absorbance at $\lambda$=490 nm) for NIH 3T3 cells exposed to the decellularized/oxidized freeze-dried human Achilles tendon allograft-derived scaffolds was 95% (1.36+/−0.31, n=10) of that observed for cells exposed to media only (1.42+/−0.31, n=10) a difference which was not statistically significant (p>0.05, FIG. 11). Cell viability determined using the Neutral Red assay (absorbance at $\lambda$=540 nm) for NIH 3T3 cells exposed to the decellularized/oxidized freeze-dried human Achilles tendon allograft-derived scaffolds was 92% (0.24+/−0.07, n=10) of that observed for NIH 3T3 cells exposed to media alone (0.22+/−0.07, n=10, positive control), a difference which was not statistically significant (FIG. 11). The decellularized/oxidized scaffold and positive control (cells only) differed significantly (p<0.001) from the values obtained for a known cytotoxic material (latex, negative control, n=10) in both assays. The absorbance observed for the negative control was also <10% of the absorbance observed for positive controls in each assay.

Example 4

Arterial Scaffolds

Figure 12:
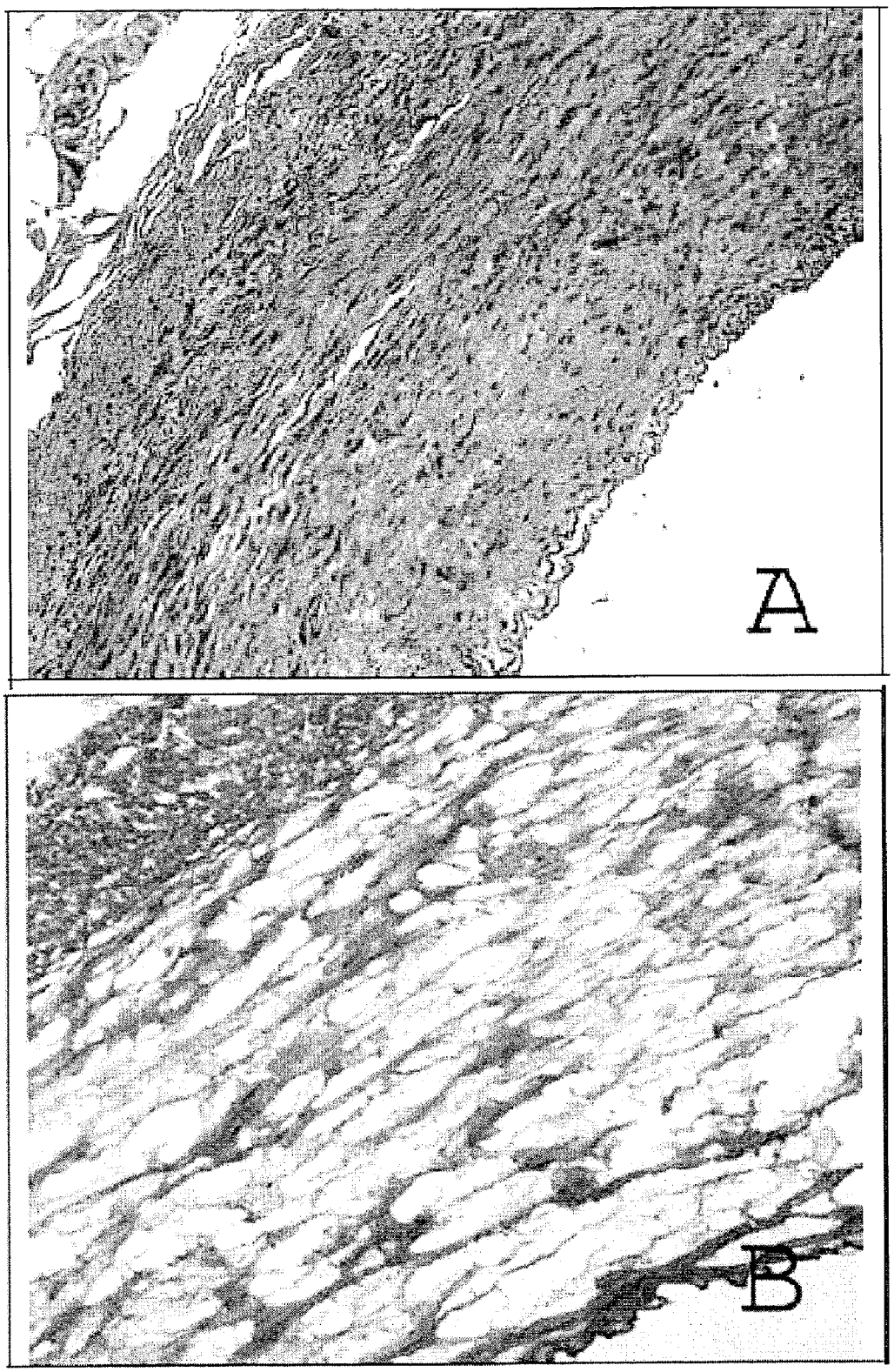
FIG. 12. Decellularization of porcine arterial segments. (A) Microscopic image of a fresh porcine carotid artery, and (B) decellularized carotid artery, both stained with H&E.

Carotid arterial segments were obtained from large pigs (400 to 600 lb). The blood vessels had an internal diameter of 3 to 4 mm and were cut into segments of approximately 50 mm in length. Vessels were washed in distilled water (D/W) for 24 hours and incubated in 0.05% Trypsin EDTA for 1 hr. Incubation in 10% FBS solution in Dulbecco's Modified Eagles Medium (DMEM) for 24 hours was used to stop the trypsin activity. The vessels were then incubated in decellularization solution (490 mL D/W, 10 mL Triton-100X, 3.4 ml ammonium hydroxide) for 3 days in a mechanical rotating shaker at 4° C. The decellularization solution was changed daily. The decellularized vessels were placed in D/W for an additional 48 hours to wash away any chemical substances from the matrix and then frozen for 24 hrs in a −80° C. freezer, lyophilized, and sterilized with ethylene oxide. Hematoxylin and Eosin (H&E) staining were performed to demonstrate that all cellular components had been removed from the matrix (FIG. 12).

Figure 13:
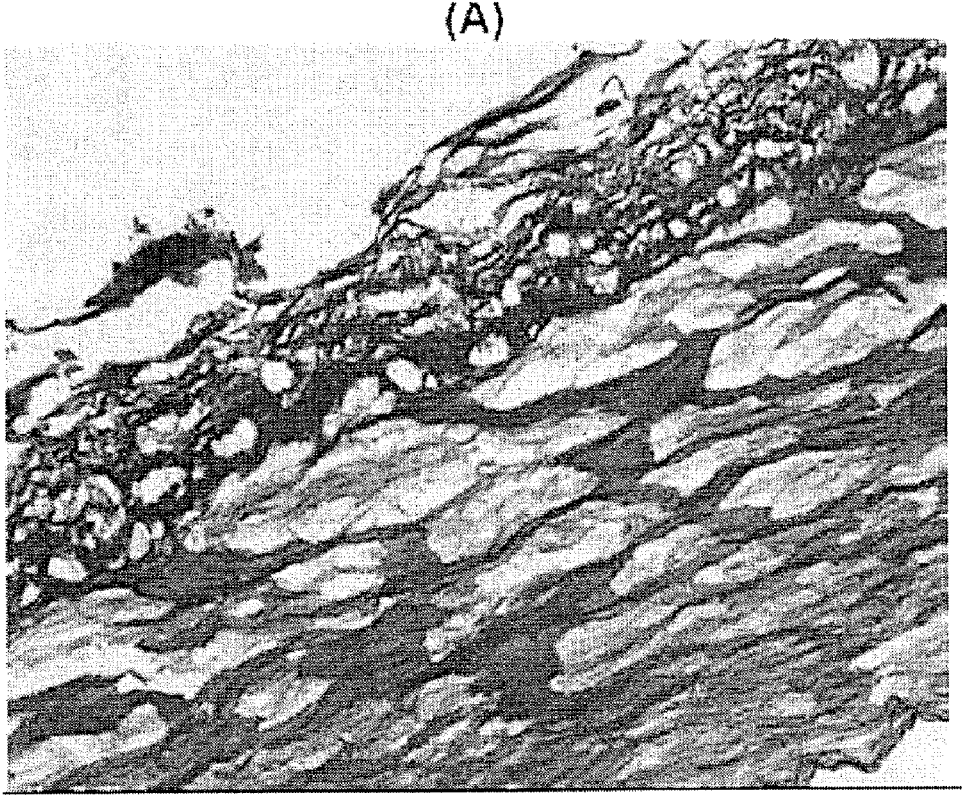
FIG. 13. The removal of adventitia layer of decellularized porcine carotid arteries. (A) Decellularized porcine carotid artery. (B) De-adventitia decellularized porcine carotid artery.
Figure 13:
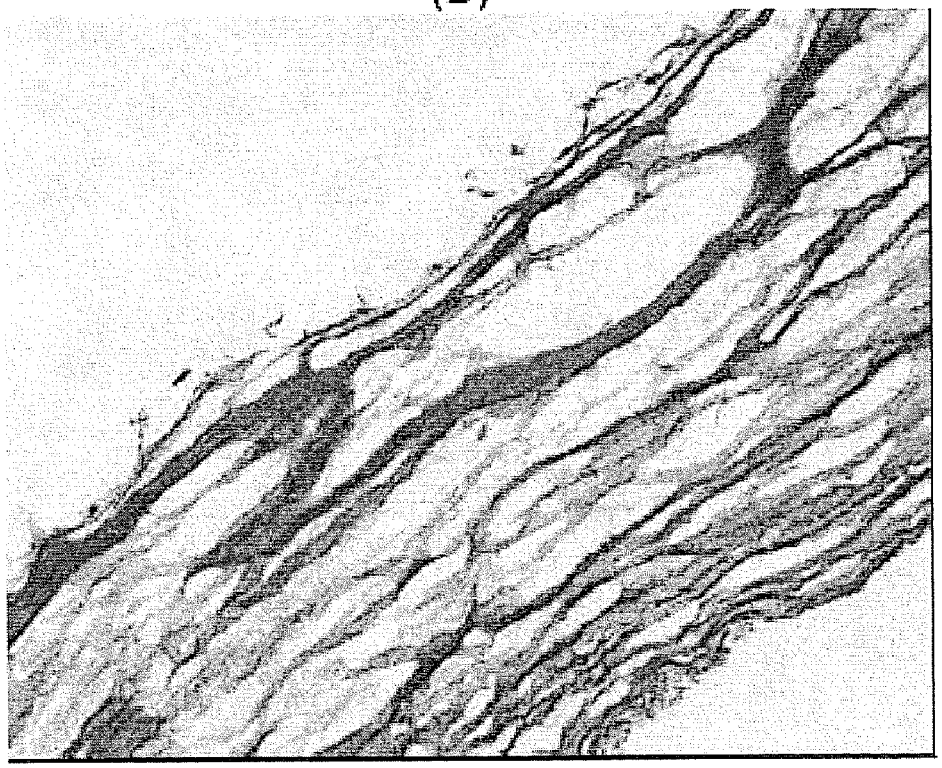

To remove the adventitia layer of the decellularized vessels, the acellular matrices were individually positioned onto an 18 Fr balloon angioplasty catheter. Once inflated, the internal diameters of the decellularized vessels were expanded to 6 mm. Using a dissecting stereo microscopic (2.5×), an incision to the sub-adventitia layer was performed with a 15 gauge blade. At this stage, the adventitia could clearly be identified from the underlying media layer. A surgical curved tip tweezer was then utilized to gently strip off the adventitia layer from the media layer. The de-adventitia decellularized porcine artery was frozen, lyophilized, and sterilized with ethylene oxide. H&E staining was performed to observe the microstructure as shown in FIG. 13.

Figure 14:
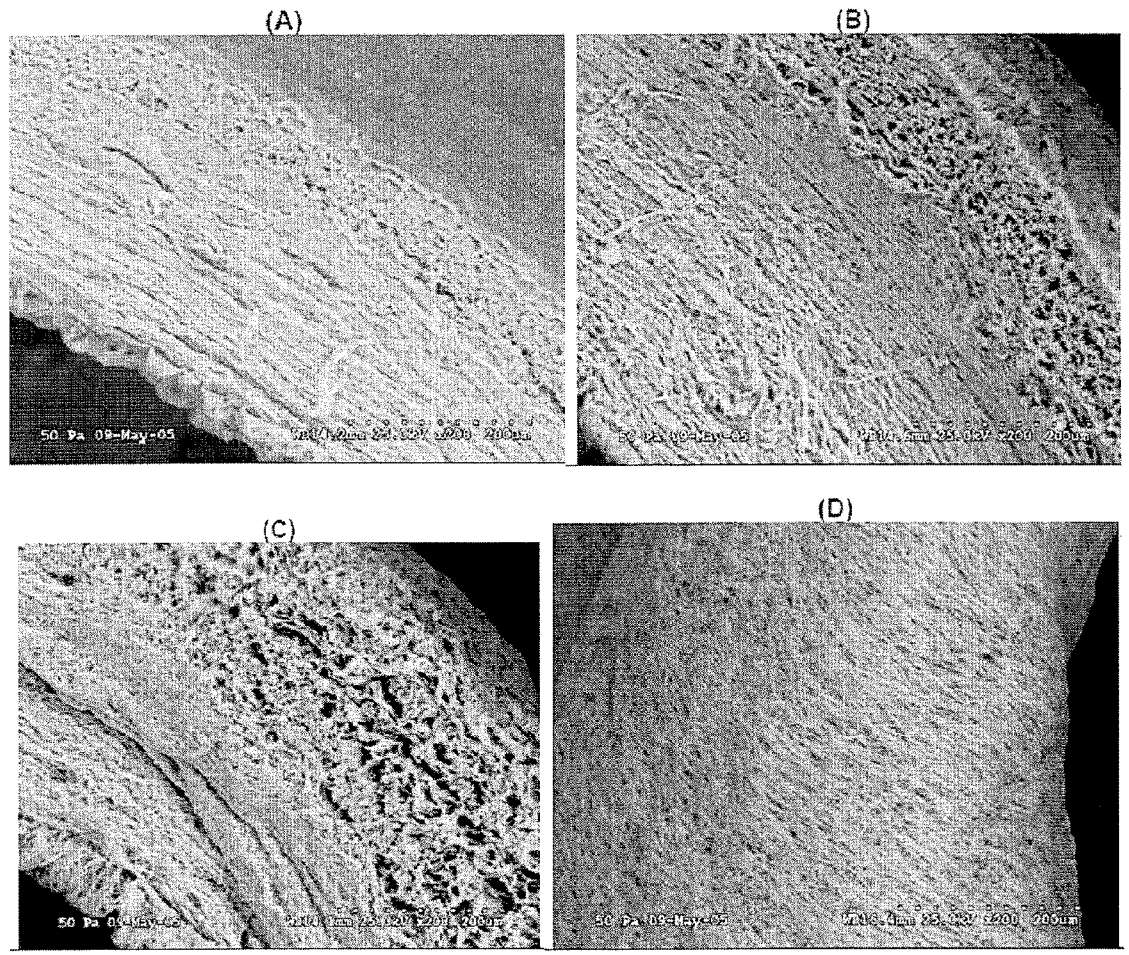
FIG. 14. SEM images demonstrating effect of increasing peracetic acid (PA) concentration on decellularized porcine carotid arteries. (A) 0% PA, (B) 3% PA, (C) 6% PA, and (D) 13% PA.

In order to increase the porosity of the acellular scaffolds, the decellularized vessels were incubated in peracetic acid (PA) for 24 hours at 37° C. in a mechanical shaker (150 RPM). Four concentrations of PA were tested that included 0%, 5%, 10%, and 15%. After 24 hours, the PA solution was removed and followed with 4 days of D/W wash that was changed daily. The vessels were then frozen, lyophilized, and sterilized with ethylene oxide. Scanning electron microscopy (SEM) was performed to analyze the effects of PA on the structural change of decellularized segments (FIG. 14).

Example 5

Meniscus Scaffolds

Medial menisci from sheep were harvested. The menisci were decellularized and treated with oxidant to increase pore size and porosity using aqueous Triton X-100 and peracetic acid. Tissue was equilibrated in phosphate buffered saline (PBS). The contralateral medial meniscus was used as a control. The central ⅓ body of each meniscus was fixed in 10% formalin and paraffin processed. Sections were cut in the coronal plane and stained with hematoxylin and eosin (H&E) for routine cellular assessment and 4',6-diamidino-2-phenylindole (DAPI) to identify residual nuclear components. Samples were assessed using light microscopy. DNA was then isolated using a commercially available kit (DNEasy, Qiagen, Valencia, Calif.). The DNA concentration in the resulting volume was used to calculate total DNA content, which is standardized using the initial dry weight of the sample. These values were averaged, a standard deviation was determined, and a comparison made using a Student's unpaired t-test with a p-value <0.05 accepted for statistical significance. The architecture of the sheep intact meniscus and the meniscus scaffold was examined using scanning electron microscopy (SEM). Specimens were examined in the coronal plane. Porosity was qualitatively compared between the intact meniscus and meniscus scaffold.

Upon gross inspection, the decellularization and oxidative treatment did not change the general shape and architecture of the meniscus. The histological findings clearly indicate a decrease in cellular and nuclear content. The H&E stained sections also show an increase in porosity. DAPI nuclear staining revealed a decrease in nuclear content in the scaffold compared to the intact fresh frozen meniscus. DNA content analysis showed a decrease in DNA content in the scaffold compared to the intact meniscus.

Figure 15:
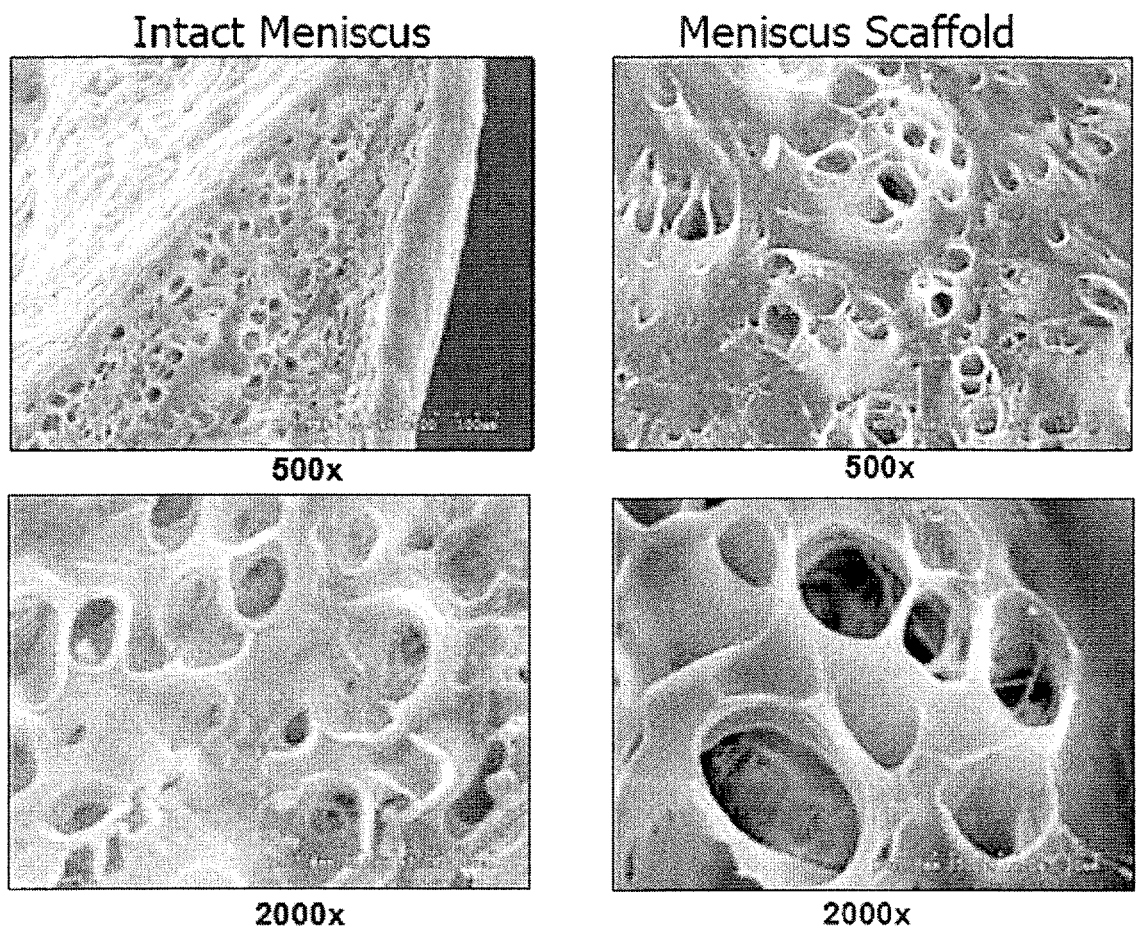
FIG. 15. SEM images comparing architecture of the intact meniscus to the scaffold. The pores of the scaffold are larger and promote cellular ingrowth.

SEM images confirmed an increase in pore size and porosity in the scaffold compared to the intact meniscus (FIG. 15). The SEM also showed that the architecture of the meniscus is intact. These results indicate that the decellularization and chemical oxidation treatments decrease DNA content in a meniscus scaffold, and that the extracellular matrix architecture of the meniscus remains intact. This process is able to increase pore size and porosity and decrease nuclear content, providing an improved scaffold that minimizes immunologic response and encourages cellular in-growth.

The foregoing is illustrative of the present invention, and is not to be construed as limiting thereof. The invention is defined by the following claims, with equivalents of the claims to be included therein.

That which is claimed is:

1. In a method of producing a bioscaffold by decellularizing a tissue to produce a bioscaffold having pores therein, the improvement comprising:
   decellularizing the tissue with an oxidant and detergent simultaneously to remove extraneous material and increase the pore size and porosity therein,
   wherein at least 70% of cells are removed from said tissue upon said decellularizing.

2. The method of claim 1, wherein said oxidant is hydrogen peroxide, peracetic acid, or a mixture thereof.

3. The method of claim 1, wherein said oxidant is in an aqueous solution at a concentration of between 1 and 32% (w/v).

4. The method of claim 1, wherein said oxidant is in an aqueous solution at a concentration of between 3 and 32% (w/v).

5. The method of claim 1, further comprising the step of washing said bioscaffold after said decellularizing step to remove residual oxidant and detergent.

6. The method of claim 5, further comprising the step of freeze-drying said scaffold following said washing step.

7. The method of claim 5, further comprising the step of sterilizing said scaffold following said washing step.

8. The method of claim 1, further comprising the step of removing adventitia from said tissue prior to said decellularizing step.

9. The method of claim 8, wherein said tissue is a blood vessel.

10. The method of claim 1, wherein said tissue is selected from the group consisting of skin, muscle, tendon, bone, meniscus, cartilage, intervertebral discs, and ligament tissue.

11. The method of claim 1, wherein said tissue is selected from the group consisting of liver, kidney, and pancreas tissue.

12. The method of claim 1, wherein said tissue is nerve tissue.

13. The method of claim 1, wherein said tissue is cartilage tissue.

14. The method of claim 1, wherein at least 80% of cells are removed from said tissue upon said decellularizing.

15. The method of claim 1, wherein at least 90% of cells are removed from said tissue upon said decellularizing.

16. A bioscaffold produced by the process of decellularizing a tissue with an oxidant and detergent simultaneously to remove extraneous material and increase the pore size and porosity therein,
  wherein at least 70% of cells are removed from said tissue upon said decellularizing.

17. The bioscaffold of claim 16, wherein said bioscaffold is sterile.

18. The bioscaffold of claim 16, wherein said bioscaffold is freeze-dried.

19. The bioscaffold of claim 16 aseptically packaged in a sterile container.

20. The bioscaffold of claim 16, wherein at least 80% of cells are removed from said tissue upon said decellularizing.

21. The bioscaffold of claim 16, wherein at least 90% of the cells are removed from said tissue upon said decellularizing.

* * * * *

UNITED STATES PATENT AND TRADEMARK OFFICE
CERTIFICATE OF CORRECTION

PATENT NO. : 7,829,108 B2
APPLICATION NO. : 11/738258
DATED : November 9, 2010
INVENTOR(S) : Van Dyke et al.

Page 1 of 1

It is certified that error appears in the above-identified patent and that said Letters Patent is hereby corrected as shown below:

On Title Page:
Item (75) Inventors: Please correct "George J. Christ, Winston-Salem"
to read -- George J. Christ, Lewisville --

Please add: Related U.S. Application Data
(60) Provisional application No. 60/794,037 April 21, 2006

Signed and Sealed this
Fifth Day of April, 2011

David J. Kappos
*Director of the United States Patent and Trademark Office*